United States Patent
Hayes et al.

(10) Patent No.: US 10,022,728 B2
(45) Date of Patent: Jul. 17, 2018

(54) PUNCTUATED MICROGRADIENTS FOR IMPROVED SEPARATIONS OF MOLECULES AND PARTICLES

(71) Applicant: ARIZONA BOARD OF REGENTS ON BEHALF OF ARIZONA STATE UNIVERSITY, Scottsdale, AZ (US)

(72) Inventors: Mark Hayes, Gilbert, AZ (US); Paul Jones, Mesa, AZ (US); Stacy Kenyon, Baltimore, MD (US); Michael Keebaugh, Mesa, AZ (US); Thomas Taylor, Tempe, AZ (US); Prasun Mahanti, Tempe, AZ (US); Sarah Staton, Washington, DC (US); Noah Weiss, Chandler, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 316 days.

(21) Appl. No.: 14/764,875

(22) PCT Filed: Feb. 3, 2014

(86) PCT No.: PCT/US2014/014495
§ 371 (c)(1),
(2) Date: Jul. 30, 2015

(87) PCT Pub. No.: WO2014/121226
PCT Pub. Date: Aug. 7, 2014

(65) Prior Publication Data
US 2015/0360237 A1   Dec. 17, 2015

Related U.S. Application Data

(60) Provisional application No. 61/759,890, filed on Feb. 1, 2013.

(51) Int. Cl.
*G01N 27/447* (2006.01)
*G01N 27/453* (2006.01)
(Continued)

(52) U.S. Cl.
CPC .......... *B03C 7/023* (2013.01); *B01L 3/50273* (2013.01); *B01L 3/502707* (2013.01);
(Continued)

(58) Field of Classification Search
CPC ....... G01N 27/44756; G01N 27/44791; G01N 27/4473; B01L 2400/0412; B03C 5/005; B03C 5/02

See application file for complete search history.

(56) References Cited

U.S. PATENT DOCUMENTS

| 5,486,335 A | 1/1996 | Wilding et al. |
| 5,964,995 A | 10/1999 | Nikiforov et al. |

(Continued)

FOREIGN PATENT DOCUMENTS

| JP | 2004-000217 A | * 1/2004 | ............. C12N 15/09 |
| WO | 2014121226 A2 | 8/2014 | |
| WO | 2014121226 A3 | 8/2014 | |

OTHER PUBLICATIONS

JPO computer-generated English language translation of Takamura et al. JP 2004-000217 A.*
(Continued)

*Primary Examiner* — Alexander S Noguerola
(74) *Attorney, Agent, or Firm* — Viksnins Harris Padys Malen LLP

(57) ABSTRACT

The present invention provides devices and methods to separate and concentrate target species. In some embodiments, a punctuated continuous microchannel or parallel processing (array-based) separations are provided, the microchannel having a plurality of sequential, constrictive (Continued)

insulating features to form a plurality of reservoirs including a first, second and third reservoir, and a plurality of constricted passageways including a first constricted passageway that connects the first reservoir to the second reservoir and a second constricted passageway that connects the second reservoir to the third reservoir. A voltage is applied to the microchannel to create different electrical fields and/or different dielectrophoresis (DEP) gradients at each of the plurality of constricted passageways in order to separate species that have differing ratios of electrokinetic mobility to dielectrophoretic mobility.

23 Claims, 13 Drawing Sheets

(51) Int. Cl.
    *B03C 7/02*     (2006.01)
    *B03C 5/00*     (2006.01)
    *G01N 30/00*     (2006.01)
    *B03C 5/02*     (2006.01)
    *B01L 3/00*     (2006.01)
    *G06F 17/50*     (2006.01)

(52) U.S. Cl.
    CPC .............. *B03C 5/005* (2013.01); *B03C 5/026* (2013.01); *G01N 27/44791* (2013.01); *G01N 30/0005* (2013.01); *G06F 17/5018* (2013.01); *B01L 2200/12* (2013.01); *B01L 2400/0424* (2013.01); *B03C 2201/26* (2013.01)

(56) References Cited

U.S. PATENT DOCUMENTS

| | | | |
|---|---|---|---|
| 5,976,336 A | 11/1999 | Dubrow et al. | |
| 6,406,893 B1* | 6/2002 | Knapp ................... | B01L 3/0262 435/287.2 |
| 6,500,323 B1* | 12/2002 | Chow .................... | B01L 3/5027 204/450 |
| 2001/0023825 A1* | 9/2001 | Frumin ............. | G01N 27/44773 204/458 |
| 2001/0025792 A1* | 10/2001 | Liu ................... | G01N 27/44782 204/451 |
| 2003/0010638 A1* | 1/2003 | Hansford ............... | B01D 57/02 204/600 |
| 2003/0070677 A1 | 4/2003 | Handique et al. | |
| 2008/0230389 A1* | 9/2008 | Ha ..................... | B01L 3/502707 204/451 |
| 2010/0006441 A1 | 1/2010 | Renaud et al. | |
| 2013/0286183 A1 | 10/2013 | Taylor et al. | |

OTHER PUBLICATIONS

Jones et al., "Blood cell capture in a sawtooth dielectrophoretic microchannel," Anal. Bioanal. Chem. (2011) 401:2103-2111.*
Illiescu et al., "A practical guide for the fabrication of microfluidic devices using glass and silicon," Biomicrofluidics 6, 016505 (2012), pp. 016506-1 to 016505-15.*
Agata, et al., "High Rate of False-Negative Results of the Rectal Swab Culture Method in Detection of Gastrointestinal Colonization with Vancomycin-Resistant Enterococci", Clinical Infectious Diseases, Jan. 2002, 34 (2)167-172.
Amory, et al., "Chemical-analysis of the surface of microorganisms by X-ray photoelectron-spectroscopy", FEMS Microbiology Letters, 1988, 49(1):107-110.
Armstrong, et al., "Separating microbes in the manner of molecules. 1. Capillary electrokinetic approaches", Anal Chem., Dec. 1999, 71(24):5465-5469.
Becker, et al., "Separation of Human Breast-Cancer Cells From Blood by Differential Dielectric Affinity", PNAS USA, Jan. 1995, 92(3):860-864.
Becker, et al., "The removal of human leukaemia cells from blood using interdigitated microelectrodes", Journal of Physics D—Applied Physics, Dec. 1994, 27(12):2659-2662.
Benjamin, et al., "The residual risk of sepsis: modeling the effect of concentration on bacterial detection in two-bottle culture systems and an estimation of false-negative culture rates", Transfusion, Aug. 2007, 47(8):1381-1389.
Burke, et al., "Influence of the semi-permdable membrane on the performance of dynamic field gradient focusing", Electrophoresis, Mar. 2010, 31(5):893-901.
Burt, et al., "Dielectrophoretic Characterization of Friend Murine Erythroleukaemic Cells as a Measure of Induced-Differentiation", Biochimica Et Biophysica Acta, Mar. 1990, 1034(1):93-101.
Castellarnau, et al., "Dielectrophoresis as a tool to characterize and differentiate isogenic mutants of *Escherichia coli*", Biophysical Journal, Nov. 2011, 91(10):3937-3945.
Chen, et al., "Insulator-based dielectrophoretic separation of small particles in a sawtooth channel", Electrophoresis, May 2009, 30(9):1441-1448.
Chou, et al., "Electrodeless dielectrophoresis of single- and double-stranded DNA", Biophysical Journal, 2002, 83(4):2170-2179.
Cong, et al., "Improved protein separation by microchip isoelectric focusing with stepwise gradient of electric field strength", J. Sep. Sci., Feb. 2009, 32(3):462-465.
Cui, et al., "Multistage isoelectric focusing in a polymeric microfluidic chip", Anal. Chem., Dec. 2005, 77(24)1878-7886.
Cummings, et al., "Dielectrophoresis in microchips containing arrays of insulating posts: Theoretical and experimental results", Anal Chem, Sep. 2003, 75(18):4724-4731.
Danger, et al., "Development of a temperature gradient focusing method for in situ extraterrestrial biomarker analysis", Electrophoresis, Aug. 2008, 29(15):3107-3114.
El Ghmari, et al. "Influence of surface cell structures on physicochemical properties of *Escherichia coli*", New Microbrologica, Apr. 2002, 25(2):173-178.
Foret, et al., "Capillary zone electrophoresis : Quantitative study of the effects of some dispersive processes on the separation efficiency", Journal of Chromatography, Oct. 1988, 452:601-613.
Gascoyne, et al., "Use of Dielectrophoretic Collection Spectra for Characterizing Differences Between Normal and Cancerous Cells", IEEE Transactions on Industry Applications, 1994, 30(4):829-834.
Giddings, "Basic approaches to separation: steady-state zone and layers", Sep. Sci. Technol., 1979, 14(10):871-882.
Giddings, et al., "Coiled columns and resolution in gas chromatography", J. Chromatogr., 1960, 3(6):520-523.
Giddings, et al., "Liquid chromatography with operating conditions analogous to those of gas chromatography", Anal. Chem., 1963, 35(13):2215-2216.
Giddings, et al., "Resolution and Peak Capacity in Equilibrium-Gradient Methods of Separation", Sep. Sci., Jun. 1971, 6(3):345-356.
Greenlee, et al., "Protein focusing in a conductivity gradient", Biotechnology Progress, Mar. 1998, 14(2):300-309.
Hamadi, et al., "The relation between *Escherichia coli* surface functional groups' composition and their physicochemical properties", Brazilian Journal of Microbiology, May 2008, 39(1):10-15.
Hofmann, et al., "Adaptation of capillary isoelectric focusing to microchannels on a glass chip", Anal. Chem., Feb. 1999, 71(3):678-686.
Hooper, et al., "Commensal host-bacterial relationships in the gut", Science, Mar. 2001, 292(5519):1115-1118.
Hsiao, et al., "Microfluidic device for capture and isolation of single cells", Proc SPIE Int Soc Opt Eng., Aug. 2010, 7759, 13 pages.
Huang, et al., "Digitally controlled electrophoretic focusing", Anal. Chem., Apr. 1999, 71(8):1628-1632.
Huang, et al., "Membrane changes associated with the temperature-sensitive P85(gag-mos)-dependent transformation of rat kidney cells as determined by dielectrophoresis and electrorotation", Biochimica et Biophysica Acta-Biomembranes, Jun. 1996, 1282(1):76-84.

(56) References Cited

OTHER PUBLICATIONS

Hutterer, et al., "Ultrahigh-voltage capillary zone electrophoresis", Anal. Chem., Apr. 1999, 71(7):1293-1297.
Jones, et al., "Blood cell capture in a sawtooth dielectrophoretic microchannel", Analytical and Bioanalytical Chemistry, Oct. 2011, 401(7):2103-2111.
Jones, et al., "Differentiation of *Escherichia coli* serotypes using DC gradient insulator dielectrophoresis", Analytical and Bioanalytical Chemistry, Jan. 2014, 406(1):183-192.
Kanner, et al., "Immunoaffinity purification of tyrosine-phosphorylated cellular proteins", J. Immunol. Methods, Jun. 1989, 120(1):115-124.
Keebaugh, et al., "Quantitative assessment of flow and electric fields for electrophoretic focusing at a converging channel entrance with interfacial electrode", Electrophoresis, Jul. 2012, 33(13):1924-1930.
Kelly, et al., "Electric field gradient focusing, Journal of Separation Science", Oct. 2005, 28(15):1985-1993.
Kenyon, et al., "Using electrophoretic exclusion to manipulate small molecules and particles on a microdevice", Electrophoresis, Apr. 2012, 33(8):1227-1235.
Latrarche, et al., "Chemical and physicochemical properties of *Escherichia coli*: variations among three strains and influence of culture conditions", Colloids and Surfaces B: Biointerfaces, Mar. 1994, 2(1-3):47-56.
Lytle, et al., "Electrophoretic mobilities of *Escherichia coli* O157:H7 and wild-type *Escherichia coli* strains", Applied and Environmental Microbiology, Jul. 1999, 65(7):3222-3225.
Meighan, et al., "Electrophoretic exclusion for the selective transport of small molecules", Electrophoresis, 2009, 30(21):3786-3792.
Meighan, et al., "Investigation of Electrophoretic Exclusion Method for the Concentration and Differentiation of Proteins", Anal. Chem., Jan. 2011, 83(1):368-373.
Olitzki, "Electric charge of bacterial antigens", Journal of Immunology, Apr. 1932, 22(4)251-256.
Pacheco, et al., "A study on the condition for differential electrophoretic transport at a channel entrance", Electrophoresis, Apr. 2007, 28(7):1027-1035.
Patent Cooperation Treaty, International Searching Authority, Search Report and Written Opinion for PCT/US2014/014495, 11 pages, May 20, 2014.
Pethig, et al., "Dielectrophoresis: Status of the theory, technology, and applications", Biomicrofluidics (vol. 4, 022811), Sep. 2010, 4(3):039901.
Petr, et al., "Analysis of microorganisms by capillary electrophoresis", Trac-Trends in Analytical Chemistry, Jan. 2012, 31:9-22.
Phillips, et al., "Enrichment of Cancer Cells Using Aptamers Immobilized on a Microfluidic Channel", Anal. Chem., Feb. 2009, 81(3):1033-1039.
Polson, et al., "Electrophoretic focusing preconcentration technique using a continuous buffer system for capillary electrophoresis", J. Microcolumn Sep., Feb 2000, 12(2):98-106.
Preira, et al., "Passive circulating cell sorting by deformability using a microfluidic gradual filter", Lab Chip, Jan. 2013, 13(1):161-170.
Pysher, et al., "Electrophoretic and dielectrophoretic field gradient technique for separating bioparticles", Anal. Chem., Jun. 2007, 79(12):4552-4557.
Ricker, et al., "Fast, reproducible size-exclusion chromatography of biological macromolecules", J. Chromatogr. A, Aug. 1996, 743(1):43-50.
Ross, et al., "Gradient Elution Moving Boundary Electrophoresis with Channel Current Detection", Anal. Chem., Sep. 2009, 81(17):7326-7335.
Ross, et al., "Microfluidic temperature gradient focusing, Analytical Chemistry", Jun. 2002, 74(11):2556-2564.
Ross, et al., "Simple Device for Multiplexed Electrophoretic Separations Using Gradient Elution Moving Boundary Electrophoresis with Channel Current Detection", Anal. Chem., Dec. 2008, 80(24):9467-9474.
Ross, et al., "Step width, spacing, and resolution in gradient elution moving boundary electrophoresis. Part 1. Theory and comparison with zone electrophoresis", Electrophoresis, Nov. 2010, 31(22):3650-3657.
Scallan, et al., "Foodborne Illness Acquired in the United States—Unspecified Agents", Emerging Infectious Diseases, Jan. 2011, 17(1):16-22.
Shackman, et al., "Counter-flow gradient electrofocusing", Electrophoresis, Feb. 2007, 28(4):556-571.
Shackman, et al., "Gradient elution moving boundary electrophoresis for high-throughput multiplexed microfluidic devices", Anal. Chem., Jan. 2007, 79(2):565-571.
Shen, et al., "Capillary isoelectric focusing of yeast cells", Anal. Chem., Oct. 2000, 72(19):4603-4607.
Srivastava, et al., "Dielectrophoretic characterization of erythrocytes: Positive ABO blood types", Electrophoresis, 2008, 29(24):5033-5046.
Staton, et al., "Characterization of particle capture in a sawtooth patterned insulating electrokinetic microfluidic device", Electrophoresis, Nov. 2010, 31(22):3634-3641.
Staton, et al., "Manipulation and capture of Aβ amyloid fibrils and monomers by DC insulator gradient dielectrophoresis (DC-iGDEP)", Analyst, Jul. 2012, 137(14):3227-3229.
Suehiro, et al., "Selective detection of specific bacteria using dielectrophoretic impedance measurement method combined with an antigen-antibody reaction", Journal of Electrostatics, Jun. 2003, 58(3-4):229-246.
Taylor, et al., "Dispersion of Soluble Matter in Solvent Flowing Slowly through a Tube", Proc. R. Soc. London A, Aug. 1953, 219(1137):186-203.
Tenover, "Potential impact of rapid diagnostic tests on improving antimicrobial use", Annals of the New York Academy of Sciences, Dec. 2010, 1213:70-80.
Tolley, et al., "Equilibrium gradient methods with nonlinear field intensity gradient: A theoretical approach", Anal. Chem., Sep. 2002, 74(17):4456-4463.
Wang, et al., "Changes in Friend Murine Erythroleukemia Cell-Membranes During Induced-Differentiation Determined By Electrorotation", Biochimica et Biophysica Acta-Biomembranes, Aug. 1994, 1193(2):330-344.
Weiss, et al., "Dielectrophoretic mobility determination in DC insulator-based dielectrophoresis", Electrophoresis, Sep. 2011, 32(17):2292-2297.
Whitman, et al., "Prokaryotes: The unseen majority", Jun. 1998, PNAS USA, 95(12):6578-6583.

\* cited by examiner

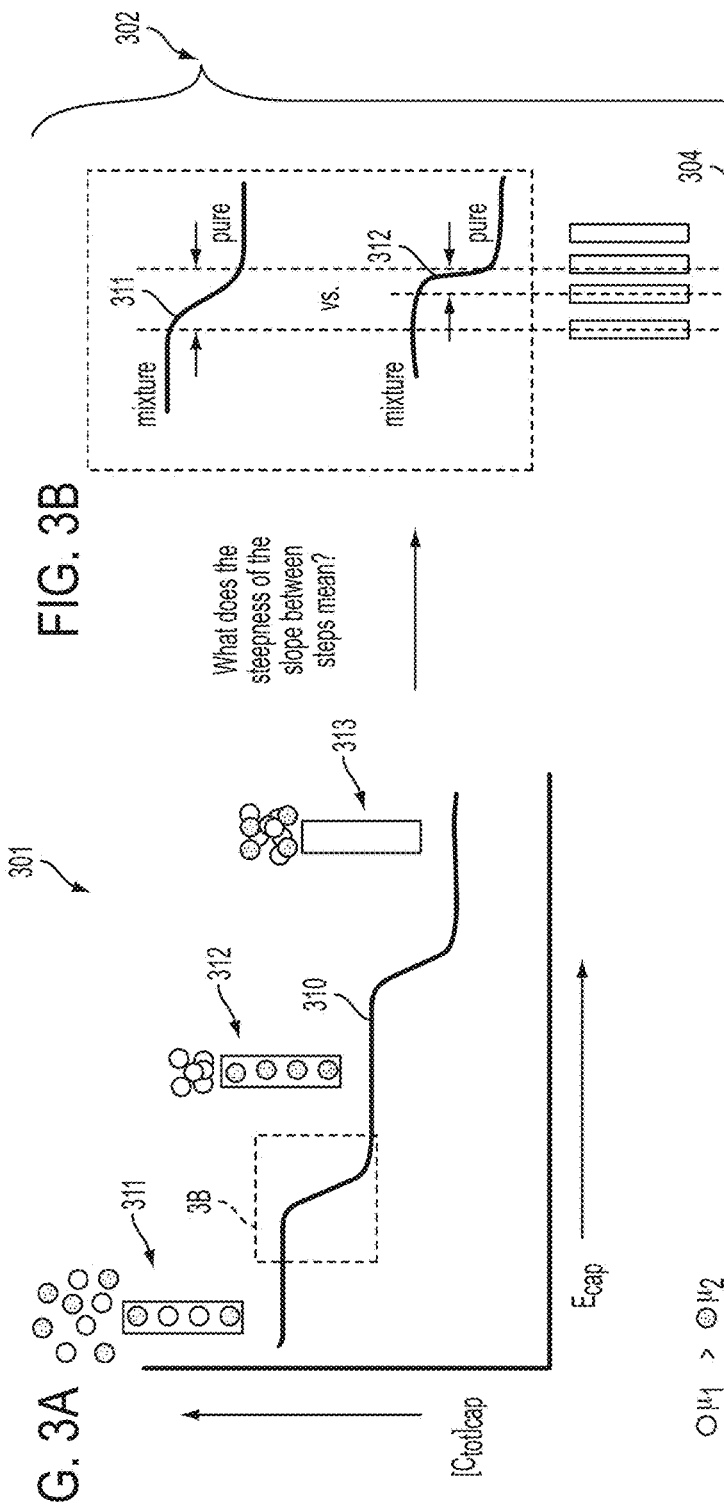
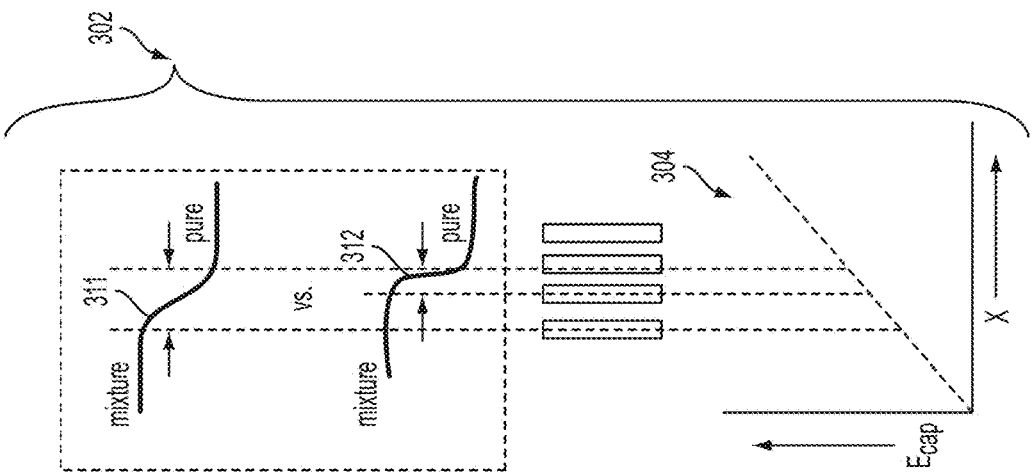
FIG. 3A
FIG. 3B

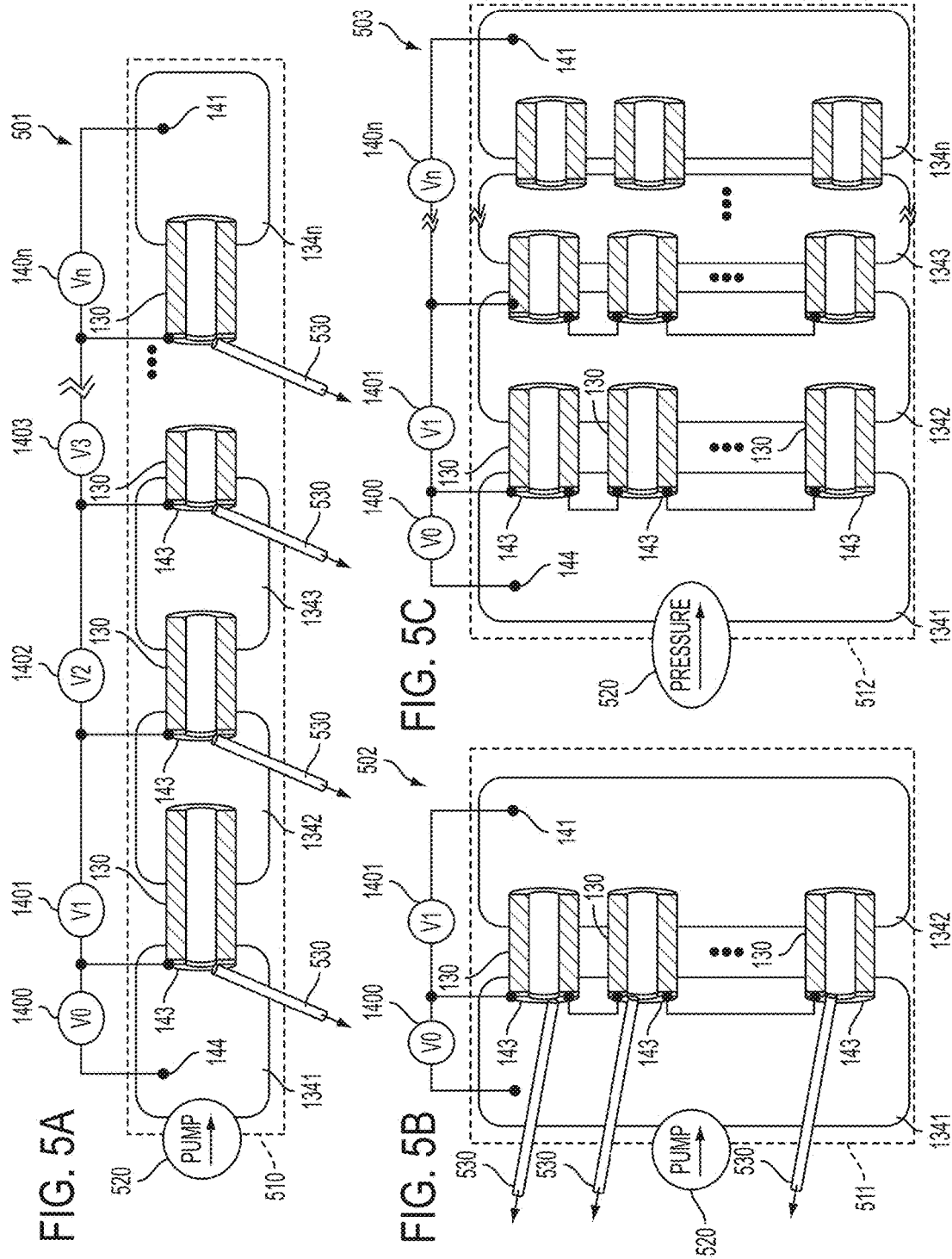

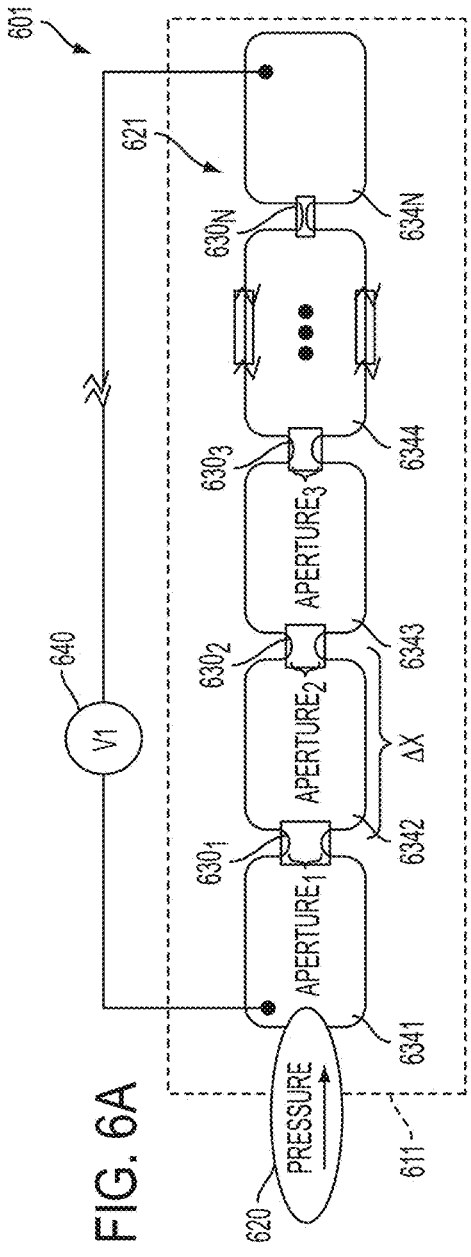
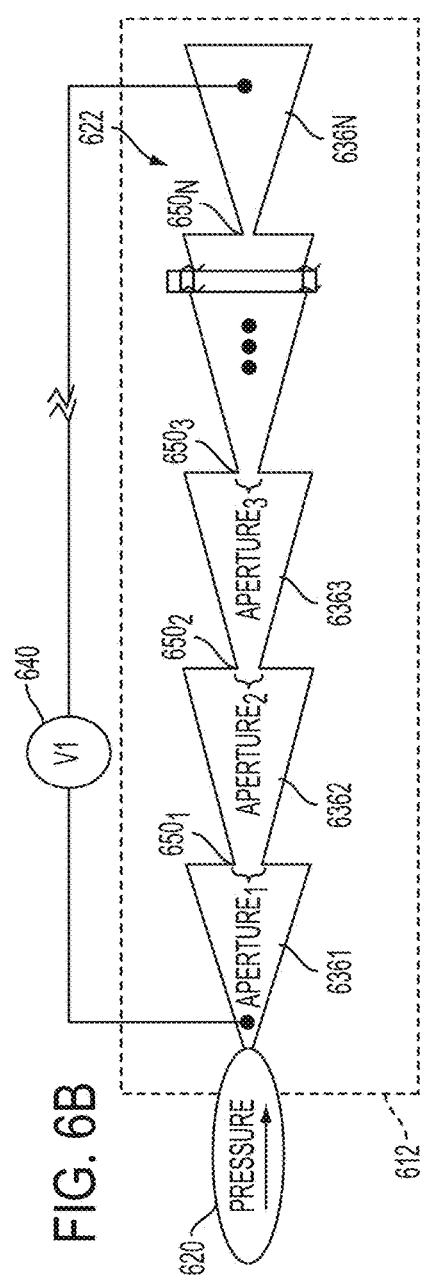
FIG. 6A
FIG. 6B

PUNCTUATED MICROGRADIENTS FOR IMPROVED SEPARATIONS OF MOLECULES AND PARTICLES

RELATED APPLICATION

This application claims priority under 35 U.S.C. 119(e) to provisional application U.S. Ser. No. 61/759,890, filed Feb. 1, 2013, which application is incorporated hereby by reference.

FIELD OF THE INVENTION

The present invention relates to devices and methods to separate and concentrate target species, and in particular to a punctuated continuous microchannel or parallel processing (array-based) separations configured to create different field at each of a plurality of constricted passageways in order to separate species that have differing ratios of focusing mobilities for two forces which can opposed one another.

BACKGROUND OF THE INVENTION

Purification strategies have evolved to cover basic extraction, precipitation, evaporation, and filtration, leading to the increased capabilities of separations science (fractionation, distillation, chromatography, electrophoresis, etc.). Core to all separations science is the basic concept of resolution: causing important components to move away from each other in time or space. Although a fundamental description of resolution (a fully general description of core processes) across all separations systems does not exist, the most successful techniques on the analytical scale are considered to be electrophoretic in nature. Early demonstrations of capillary-based and microchip-based electrophoresis have shown extraordinary resolution using high fields, showing deuterated vs. hydrogenated and submillisecond separations fully based on interactions of the analyte with the solvent/buffer and an applied field. These results were generally obtained in systems operating in a linear mode—spreading and diluting a mixture out along a single axis.

SUMMARY OF THE INVENTION

The present invention provides devices and methods to separate and concentrate target species of target material. In some embodiments, a punctuated continuous microchannel is provided, the microchannel having a plurality of sequential or parallel features, which form a plurality of reservoirs including a first, second and third reservoir, and a plurality of constricted passageways including a first constricted passageway that connects the first reservoir to the second reservoir and a second constricted passageway that connects the second reservoir to the third reservoir. A force is induced to the microchannel to create different gradients at each of the passageways in order to separate species that have differing ratios of mobilities.

In some embodiments, the present invention provides a punctuated microgradient device that includes a substrate having a first continuous microchannel that is patterned with a plurality of sequential, constrictive insulating features to form a plurality of reservoirs including a first, second and third reservoir, and a plurality of constricted passageways including a first constricted passageway that connects the first reservoir to the second reservoir and a second constricted passageway that connects the second reservoir to the third reservoir, wherein the microchannel has walls that are electrically insulative; and a first electrode and a second electrode both operatively coupled to the first microchannel and configured to establish an electric field E within the microchannel. In some embodiments, the first electrode is operatively coupled to the first reservoir along the length of the first microchannel and the second electrode is operatively coupled to the last reservoir along the length of the first microchannel, and a voltage is applied between the first electrode and the second electrode. In some such embodiments, one or more additional electrodes are operatively coupled to the first microchannel along the length of the first microchannel between the first electrode and the second electrode. In some embodiments, a pump is connected to apply a pressure difference between the first reservoir and the last reservoir of the first microchannel in order to urge a flow of material through the first microchannel, wherein the apparatus is configured to establish different electric fields and/or different dielectrophoretic gradients at each of the plurality of constricted passageways along the first microchannel. In some embodiments, a plurality of microchannels, each substantially the same as the first microchannel, are fabricated in a single substrate.

In some embodiments, the present invention provides a method of separating particles. This method includes providing a substrate having a first continuous microchannel that is patterned with a plurality of sequential, constrictive insulating features to form a plurality of reservoirs including a first, second and third reservoir, and a plurality of constricted passageways including a first constricted passageway that connects the first reservoir to the second reservoir and a second constricted passageway that connects the second reservoir to the third reservoir, wherein the microchannel has walls that are electrically insulative; and applying a first local electrical field $E_1$ in the first constricted passageway and a second local electrical field $E_2$ in the second constricted passageway, and wherein a magnitude of the first local electrical field $E_1$ is greater than the second local electrical field $E_2$. Some embodiments of the method further include establishing a first local dielectrophoresis (DEP) gradient, $(d\nabla|E|^2/dx_1)_{local}$ at the first constricted passageway and a different second local dielectrophoresis (DEP) gradient, $(d\nabla|E|^2/dx_2)_{local}$ at the second constricted passageway, wherein $x_1$ is a length parameter of the first constricted passageway, $x_2$ is a length parameter of the second constricted passageway.

BRIEF DESCRIPTION OF THE FIGURES

FIG. 3A is a schematic graph 301 showing concentration curve 310 in a punctuated-microgradient device, according to some embodiments of the present invention.

FIG. 3B is a schematic graph 302 comparing a shallow-sloped concentration curve 311 to a steep-sloped concentration curve 312 (and a curve 304 of $E_{cap}$ versus position X) in a punctuated-microgradient device, according to some embodiments of the present invention.

FIG. 5A is a schematic diagram of a serial electrophoretic exclusion device 501, according to some embodiments of the present invention.

FIG. 5B is a schematic diagram of one stage of a parallel electrophoretic exclusion device 502, according to some embodiments of the present invention.

FIG. 5C is a schematic diagram of a parallel-and-serial electrophoretic exclusion device 502, according to some embodiments of the present invention.

FIG. 6A is a schematic diagram of a serial electrophoretic exclusion device 601, according to some embodiments of the present invention.

FIG. 6B is a schematic diagram of one stage of a parallel electrophoretic exclusion device 602, according to some embodiments of the present invention.

DETAILED DESCRIPTION OF THE INVENTION

Figure 1A:
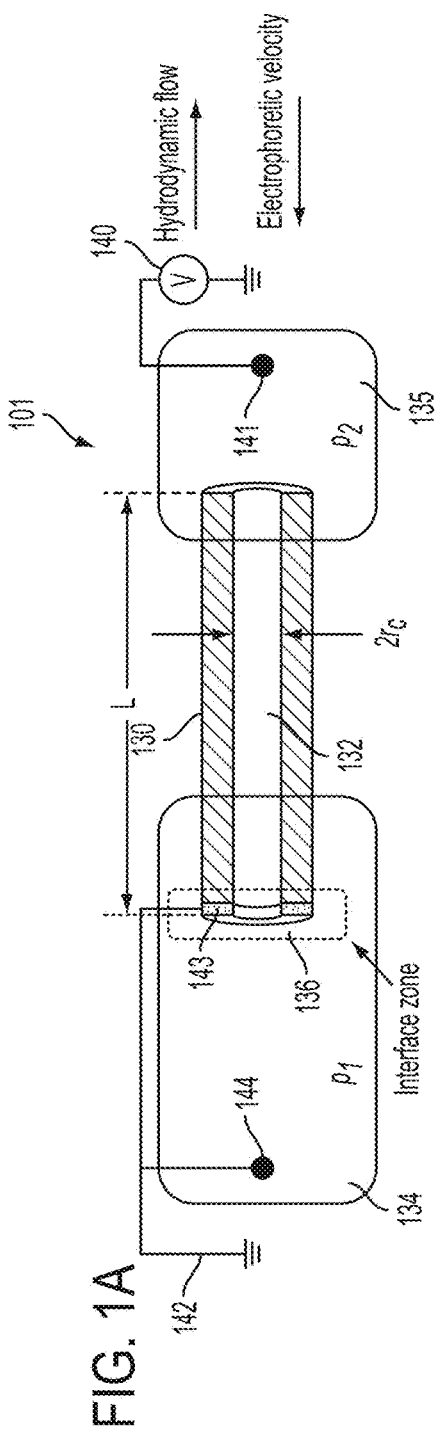
FIG. 1A is a schematic diagram of a punctuated-microgradient device 101, according to some embodiments of the present invention.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention.

The leading digit(s) of reference numbers appearing in the Figures generally corresponds to the Figure number in which that component is first introduced, such that the same reference number is used throughout to refer to an identical component which appears in multiple Figures. Signals and connections may be referred to by the same reference number or label, and the actual meaning will be clear from its use in the context of the description.

In the present invention, as in other steady-state focusing (isoelectric focusing (IEF) being the most popular) techniques, restoring forces are present. The velocity change away from the balance point is a function of charge (z) and the field strength (E) for IEF. For the present invention, the gradients can be flow, electric field (electrophoretic) or field gradients (dielectrophoresis (DEP)). The present invention's concept can be extended to any forces that can be configured into punctuated microgradients.

In certain embodiments, the present invention provides a new approach for separating components enabled by the short length-scale of microdevices and strong local field gradients. Concentrating a target species, while simultaneously separating it away from interferents, is a goal of the present invention. To accomplish this, significant gradients are often induced (see FIG. 1A). These can be chemical potential (solvents, phases, surfaces, molecular recognition, pH, etc.) or applied external fields (flow, electric, magnetic, gravity, etc.). Electrophoretic exclusion (EpE) and gradient dielectrophoresis (gDEP), which use electric-field gradients, are presented in detail here. Electrophoretic exclusion uses a constant flow field with an induced electric-field gradient, differentiating species based on electrophoretic mobility. Gradient dielectrophoresis sets electrophoresis against dielectrophoresis. This can be accomplished because electrophoresis is linear with the electric field (and directional), whereas dielectrophoresis is a function of the gradient of the field squared (non-directional with charge). While developing EpE, extraordinary results were continuously observed which were immediately discounted as not possible. When placing an electric-field gradient across a flow path with charged species present, the target focused in a very narrow band—far too narrow from our point of view and compared to any reports in the literature. Similarly, for the dielectrophoresis, unexpectedly narrow features were seen for concentration of particles, along with the differentiation of otherwise homogeneous particle populations (monodisperse, homogeneous zeta potential).

We have developed an underlying theoretical framework for both projects. It turns out that they were largely equivalent in a non-obvious way: the core feature that generated these unexpected results is the creation of punctuated microgradients separated by flat field zones. This uniquely minimizes the effects of diffusion by dramatically increasing the local restoring forces. The local gradients restore, immediately, any target which diffuses from its balance point 133 (FIG. 1B). As a result, resolution increases by a factor tied to the square root of the local gradients, while the absolute magnitude of the applied field is minimized—both of these extend the dynamic range compared to traditional systems. The peaks are more narrow and the range of applied field is extended.

Perhaps even more important, because this focusing occurs at a narrow interfacial zone (a few microns wide), it can be accomplished in parallel or in series or both (see FIGS. 5A, 5B, and 5C). This opens up several new venues for exploitation. Traditional separation strategies can be accomplished with higher resolution and a smaller footprint. Since this technique works in parallel, an array format can be envisioned. The array can be dynamic and programmable while simultaneously collecting specific analytes at higher resolution than is available from any traditional technique. Speeds of separations are also dramatically increased since the differentiation occurs at the entrance interface and not within a column or tube. These principles can be applied to particles up to ten microns in diameter and down to single small molecules—spanning a tremendous range of the targets found in real-world samples.

The underlying theoretical principles are described and examples provided for flow/electric field and electrokinetic/dielectrophoretic devices in a microfluidic format. With these techniques, we have shown unique capture of red blood cells, specific strains of bacteria, and polystyrene particles, along with focusing of proteins, protein aggregates (amyloids), and small molecules (fluorescent dyes).

Punctuated Microgradient Device
Methods of Separation

EXAMPLE 1

Introduction

Analyzing complex samples, such as those from biological and environmental sources, frequently requires the techniques from the field of separation science to first isolate the species of interest. Many of the targets are related, but unwanted, species that possess extremely similar properties for which the subtle differences are biologically or environmentally important. In these cases, to be able to adequately study the samples, separations are performed using common techniques such as chromatography (size exclusion and affinity) [1, 2] and electrophoresis.

Although these common techniques are extensively used for complex samples, they result in diffusion and dilution over the course of their separation. Equilibrium gradient methods, in contrast, utilize separating and focusing forces simultaneously to effectively counteract dispersion, including diffusion, resulting in better detection limits [3]. Isoelectric focusing (IEF), an example of a well-known equilibrium gradient technique, employs a pH gradient with a constant electric field, to separate species when they reach their isoelectric points (pI's) [4-6]. Other more recent examples of equilibrium gradient techniques include electric-field-gradient focusing (EFGF) methods [7-13]. EFGF techniques have a hydrodynamic counterflow through a channel and an electric field gradient along the length of the channel. Species with differing electrophoretic velocities are isolated at their zero-force points, where their electric-field-induced velocity is equal to, and opposite of, the bulk flow velocity. As with other equilibrium gradient methods, species in EFGF separations are therefore isolated and concentrated simultaneously.

A successful separation is usually defined by generating adequate resolution, more so for analytical scale or complex samples, compared to some well-characterized samples of preparative scale systems where this requirement can be relaxed. The resolving capabilities of the more common separations techniques, including chromatography [14, 15], IEF [3], and capillary-zone electrophoresis (CE) [16], are well-established and experimentally confirmed. More recently, resolution equations for EFGF techniques have been developed. Tolley et al. described the resolution of electromobility focusing [17] and Kelly and Woolley described EFGF resolution by comparing the focusing effects near the zero-force point to a spring and invoked the mathematics of Hooke's Law to describe the forces [9]. Ultimately, they described the properties of EFGF as it successfully increases sample concentration and separates species with similar electrophoretic mobilities.

Reducing dimensions to the microscale has the potential to improve EFGF devices. Gradient elution moving-boundary electrophoresis (GEMBE), another equilibrium gradient technique, has been used to successfully perform electrophoretic separations in short channels [18-20]. Ross developed a theoretical framework to describe the resolving capability of GEMBE and compared it to the resolving power of CE, showing that GEMBE separations could be performed on the same time-scale and provide similar resolution as CE separations [21].

Electrophoretic exclusion, somewhat related to EFGF techniques, is a separation method first introduced by Polson et al. as an enrichment scheme [22]. In this technique, briefly, a hydrodynamic fluid flow through a channel is used to counter the electrophoretic velocity of the species of interest. When the electrophoretic velocity is greater than or equal to the countering hydrodynamic flow, the species are excluded in a buffer reservoir, just outside of a channel. Unlike EFGF techniques, the electric field remains constant in the channel, and a sharp local gradient is instead initiated right at the channel entrance, allowing for highly localized separation just outside of the channel entrance in bulk solution rather than in a channel. This difference, though it may seem subtle, allows for parallelization to positively affect the overall resolution capabilities.

The success of electrophoretic exclusion has been demonstrated experimentally using both mesoscale [22-25] and microscale [26] devices. The technique has proven to be applicable to a variety of analytes with various properties and sizes, including small molecules, polystyrene microspheres, and proteins. Additionally, studies have been conducted to model the physicality and actions of the electrode/solution/channel interface [27]. However, a thorough study of the resolution capabilities of the technique from a traditional separations-science point-of-view has not yet been conducted. Resolution and dynamic range of electrophoretic exclusion will be defined using common dimensionalities, materials, and electric potential magnitudes of current devices, thereby developing a foundational framework to interrogate the resolving power of electrophoretic exclusion enabled by the localized microgradient. By extension, since the interface can be parallelized or placed in series, a variety of new capabilities can be envisioned.

2. Theory

For comparison to other electrophoretic techniques (traditional and gradient), resolution is described in terms of closest electrophoretic mobilities of two species that can be differentiated—one fully excluded and one fully entering the channel. Resolution, R, will be described as:

$$R = \frac{\Delta X}{4\sigma} \quad (1)$$

In this equation, ΔX is the distance between separated elements and σ is the standard deviation of the elements. Both of these variables are easily defined within traditional separations, with ΔX and σ described in terms of distance or time reflecting the distribution of the separated concentration profiles. The interface under study here does not produce traditional concentration profiles, or peaks, and the distance between two separated species cannot be defined in a traditional sense. However, this interface does provide for separation of species and properties of the interface and the physicality of the target species allow for direct quantitative comparison to be made to other techniques.

To provide a basis for discussion, the principles of exclusion and conventions of the model are briefly outlined. This discussion focuses on the centerline, and other factors (laminar flow) will be considered. Flow is established inward, towards, and within a channel, and an electric field is introduced within the channel itself only, introducing a gradient at the entry region. Electrophoretic exclusion occurs when the electrophoretic velocity (product of the electrophoretic mobility and the electric field) of a species is opposite and greater than or equal to the fluid velocity into the channel. Under these conditions, the species is excluded from entering the capillary. Species with electrophoretic velocities smaller than the opposing fluid flow will instead flow through the channel.

Figure 1B:
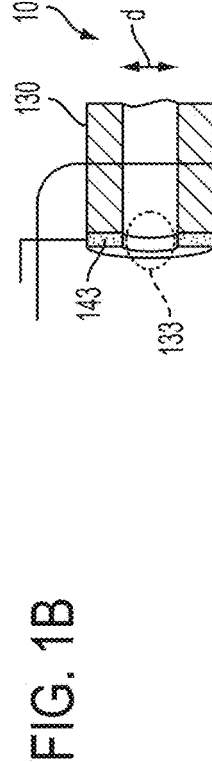
FIG. 1B is a schematic diagram of the geometry 102 of one end of the flow channel in punctuated-microgradient device 101, according to some embodiments of the present invention.

In one embodiment, a device description is included (FIG. 1A). The materials and details are not central to the theoretical approach, as it is a general model, but this is presented to aid in communication and establish physicality for later discussion. The device is composed of two reservoirs, a fluid-source reservoir 134 and a fluid-destination reservoir 135 connected with a capillary 130. Bulk flow is from left to right through the system 101, driven by a pressure differential in the reservoir chambers 134 and 135. In some embodiments, the end of the capillary 130 (or its channel 132) in chamber 134 contains an integral electrode 143 that is constructed by removing approximately 3 mm of polyimide coating from a capillary tip and then sputtering with 30 nm of Ti and 50 nm of Pt. Silver conductive epoxy is then used to physically connect the tip of the sputter-coated capillary to a 1-cm piece of Pt wire. Power can be applied to the wire (e.g., by connecting a voltage supply 140 between voltage electrode 141 in reservoir 135 and an electrical ground 142, and connecting the electrical ground to the electrode 143 at the left-hand tip of capillary 130) and when potential is applied, the tip 136 of the capillary 130 acts as an electrode. As a result of the capillary tip electrode and the Pt wire in the reservoir, no potential field exists in the bulk of reservoir 134. In some embodiments, a ground electrode 144 (electrically connected to capillary-tip electrode 143) is placed in chamber 134, and a voltage electrode 141 is placed in reservoir 135. The area of interest, where exclusion occurs, is in chamber 134, at the fluid-entry region 133 or interface of the capillary 130.

2.1. Defining the Interface

Exclusion occurs when the electrophoretic velocity of a species (v) is greater than, or equal to, the opposing hydrodynamic flow velocity (u):

$$v \geq -u \quad (2)$$

The calculated fluid flow velocity (u) through the system is given by:

$$u = \frac{\Delta p r_C^2}{\mu L_n} \quad (3)$$

where Δp is the pressure difference between the two chambers, $r_c$ is the radius of the capillary, L is the length of the capillary, and n is the viscosity of the buffer. Electro-osmosis is suppressed for the purposes of this model, but it can be added trivially without changing u, but could reduce Taylor dispersion (addressed below).

Consider two arbitrarily closely related targets with electrophoretic mobilities $\mu_1$ and $\mu_2$ (ostensibly, one excluded, the other not), the average electrophoretic mobility ($\mu_{ave}$) is:

$$\mu_{ave} = \frac{(\mu_2 + \mu_2)}{2}. \quad (4)$$

The electrophoretic velocity is the product of the electrophoretic mobility and the local electric field strength (E), so the average electrophoretic velocity ($v_{ave}$) of the target pair is:

$$v_{ave} = \mu_{ave} E \quad (5)$$

2.2. Structure of Flow and Electric Fields Near/Within the Interface

Figure 1C:
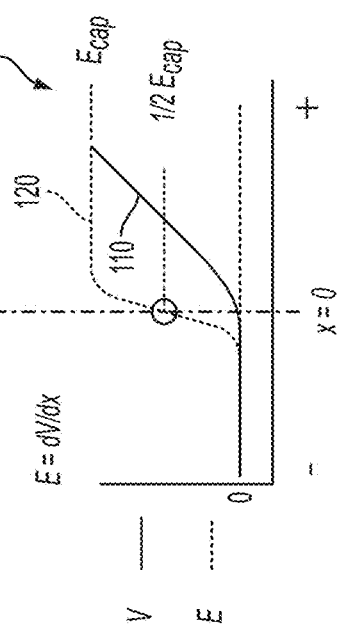
FIG. 1C is a schematic graph 103 showing curve 110 and curve 120 correlated to geometry 102 of FIG. 1B at one end of the flow channel in punctuated-microgradient device 101, according to some embodiments of the present invention.

In electrophoretic exclusion, the electric field is initiated at the electrode-channel entrance interface; there is no field in the reservoir 134 away from the capillary entrance 133. Within the body of the capillary, the electric field (curve 120 in FIG. 1C) is constant and set at $E_{cap}$ (FIGS. 1B & 1C). The voltage (curve 110 in FIG. 1C) goes from zero just outside the capillary at the left end, to a voltage near the voltage applied to electrode 141 in reservoir 135 since the small-diameter of the capillary will have a constant and much higher electrical resistance than the bulk fluid in reservoir 135, and thus the majority of voltage drop is in the capillary. Immediately outside the capillary entrance 133, in the middle of the linear electric field gradient, where $E=\frac{1}{2}E_{cap}$, $v_{ave}$ is defined as the opposite of the bulk flow:

$$v_{ave} = -\frac{1}{2} E_{cap} \mu_{ave} \quad (6)$$

Assuming $\mu_1$ is greater than $\mu_2$, at this point, the species with $\mu_1$ is completely excluded (effects of dispersion addressed below), while the species with $\mu_2$ is not excluded, but allowed to travel past the interface and down the length of the capillary. Flow rate near the entrance is assumed to be constant over the length of the scale of the electric field gradient (penetrating ~½ the capillary diameter into the reservoir).

2.3. Steady-state, Fully Developed Concentration Profile

Figure 2A:
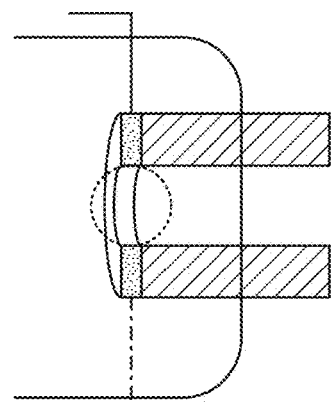
FIG. 2A is another schematic diagram of the geometry 102 of one end of the flow channel in punctuated-microgradient device 101, according to some embodiments of the present invention.
Figure 2B:
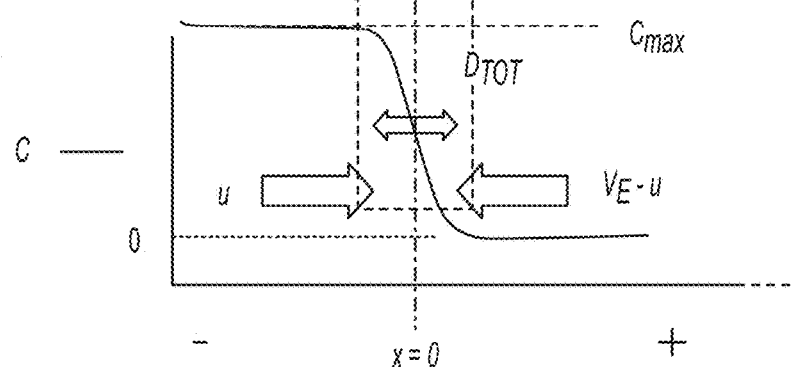
FIG. 2B is a schematic graph 202 showing concentration curve 210 correlated to geometry 102 of FIG. 2A at one end of the flow channel in punctuated-microgradient device 101, according to some embodiments of the present invention.
Figure 2C:
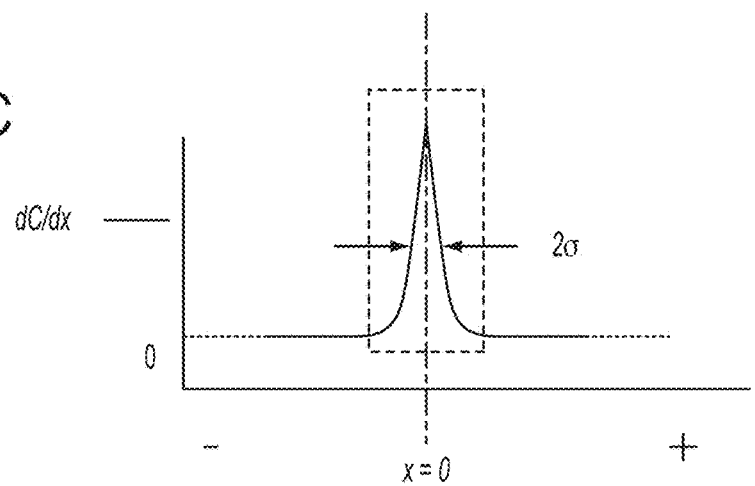
FIG. 2C is a schematic graph 203 showing change-in-concentration-versus-X curve 220 correlated to geometry 102 of FIG. 2A at one end of the flow channel in punctuated-microgradient device 101, according to some embodiments of the present invention.

The concentration profile for a fully excluded analyte is described (FIG. 2). The maximum concentration is in the reservoir, which decreases to zero at the channel entrance (FIG. 2B). The area of most interest is the slope across the interface. The steepness of the slope varies, depending on focusing and dispersive forces and defines a characteristic variance.

Using the practice of Giddings, a steady-state separation has a constant concentration profile with time (dc/dt=0), where, in this case, the dispersion forces are equivalent and opposite to flow/electric field forces [28]. The structure of this concentration profile at steady state can be described by an error function that also lends itself to simple assessment of the variance of the concentration profile of this interfacial region [21]. The derivative of an error function is a Gaussian profile with a characteristic variance. This variance provides a standard means of comparison for steady-state methods and is defined by including all dispersive forces ($D_{TOT}$) competing with the restorative forces and is equal to [3]:

$$\sigma^2 = \frac{D_{TOT}}{\text{change in velocity with position}} \tag{7}$$

The total dispersive forces cause band broadening, while focusing forces reduce the bandwidth. $D_{TOT}$ is equal to a. $D_{TOT}$ includes diffusion ($D_{diff}$) and Taylor-Aris dispersion [29]:

$$D_{TOT} = D_{diff} + \frac{u^2 d^2}{192 D_{diff}} \tag{8}$$

To understand the local velocity of the target species across this interfacial zone, the approach (and notation) given by Giddings [28] that states the overall transport (W) in the system is:

$$W = U + v \tag{9}$$

where W is the overall component velocity, U is the drift velocity due to external fields (field-induced velocity), and v is the flow velocity. For electrophoretic exclusion, substitute, −u for v (eqn. 1) so that:

$$W = U - u \tag{10}$$

In this case, only U varies with x, so the equation can be rewritten as:

$$W = ax - u \tag{11}$$

where a is change in velocity (slope) with respect to x, describing the focusing effects (field gradient dE/dx at the capillary entrance). Within the bulk reservoir 134, at negative values of x and outside the interface zone 133, the target species move at an average velocity of u or less. The electrophoretic velocity of the target species is less than the flow velocity due to small or nonexistent E. At exactly x=0 (the capillary entrance/electrode solution interface, FIG. 2), the average velocity of the target species is zero because u is exactly offset by $\frac{1}{2}E_{cap}\mu_{ave}$. At x values above zero (within the capillary, past the interface zone 133) the velocity is $u+\mu E_{cap}$.

The change in the electrophoretic velocity near the entrance, a, is:

$$a = \frac{\mu_{ave} dE}{dx} \tag{12}$$

and therefore $$W = \mu_{ave} \frac{dE}{dx} x - \frac{1}{2} \mu_{ave} E_{global} \tag{13}$$

The local slope of the electric field (dE/dx) can be approximated and linearized by the change in the field across the interface divided by the diameter of the entrance. Noting eqns. 5, 6 and 10, variance is:

$$\sigma^2 = \frac{D_{diff} + \frac{u^2 d^2}{192 D_{diff}}}{\mu_{ave} \frac{dE}{dx}} \tag{14}$$

and standard deviation is equal to:

$$\sigma = \sqrt{\frac{D_{diff} + \frac{u^2 d^2}{192 D_{diff}}}{\mu_{ave} \frac{dE}{dx}}} \tag{15}$$

resulting in a form very similar to other tradition gradient models, but with the local gradient at the entrance rather than the global gradient of standard techniques [9].

2.4. Determining the Two Closest Resolvable Species

A construct must be created to determine the closest two electrophoretic mobilities that can be resolved with these associated variances. In this system, the linearized local slope (dE/dx) at the entrance (approximated by $E_{cap}$ divided by the diameter, d) controls what can and cannot enter the capillary. This must be varied in time or space. It is easier to conceptualize slowly varying the capillary's electrical potential and monitoring what can enter the capillary, but this strategy omits the inherent advantages of the local gradient by slowly releasing any collected materials at the interface and smearing out the narrow concentration gradients. Alternatively, we choose to model in space, where a construct is created that sets $E_{cap}$ between adjacent capillary entrances as a direct function of the distance between the centerline of those capillaries (FIG. 3). This solves three problems: 1) it retains the advantages present in the local gradient at each capillary entrance, 2) sets a physically meaningful construct reflective of real experiment apparatus, and 3) provides a function definition of ΔX easily conceptualized and tested.

A short description of the construct is presented as an example. Three channels are considered with three different $E_{cap}$ values. One channel 311 has a small enough $E_{cap}$ that neither species will be excluded from the capillary entrance (FIG. 3A left), allowing both species to flow through the capillary with the hydrodynamic flow (resulting in the highest total concentration in the channel). A second channel 312 has an increased $E_{cap}$, such that the species with the larger mobility (represented with gray circles) are excluded (FIG. 3A center), producing an increased concentration of that larger mobility species immediately outside of the capillary and complete passage of the other (represented by the black circles) through the channel 312. In a third channel 313, $E_{cap}$ is such that the species with the smaller mobility will also be completely excluded (FIG. 3A right), and both species are completely prevented from entering the channel 313. In this case, the applied field (E=dV/dx) is too large to achieve separation of the specified analytes.

Conceptually, the sharper the transition between channel entrances, the closer the capillaries can be in (in terms of $\Delta X$ and $E_{cap}$) and still achieve successful differentiation (FIG. 3B). The change in $E_{cap}$ between the entrances defines $\Delta dE/dx$, or the change in $dE/dx$, between to nearest-neighbor channel entrances:

$$\Delta X = \frac{\Delta v}{\frac{du}{dx}} = \frac{\Delta \mu E_{ave}}{\frac{1}{2}\mu_{ave}\left(\Delta \frac{dE}{dx}\right)} \quad (16)$$

Note this differentiation is for only one of these 'steps' (FIG. 3) and resolution can be described by:

$$R = \frac{\Delta X}{4\sigma} = \frac{\frac{\Delta \mu E_{ave}}{\frac{1}{2}\mu_{ave}\left(\Delta \frac{dE}{dx}\right)}}{\sqrt[4]{\frac{D_{diff} + \frac{u^2 d^2}{192 D_{diff}}}{\mu_{ave}\frac{dE}{dx}}}} = \frac{\Delta \mu E_{ave}\sqrt{\frac{dE}{dx}}}{\sqrt[2]{\mu_{ave}}\Delta \frac{dE}{dx}\sqrt{D_{diff} + \frac{u^2 d^2}{192 D_{diff}}}} \quad (17)$$

which suggests several things, including a steep gradient at the entrance and minimizing the difference between these local gradients in adjoining capillaries would maximize resolution.

The smallest change in electrophoretic mobilities is identified as the best resolution for the technique, so the resolution was solved for $\Delta \mu$:

$$\Delta \mu = \frac{R \cdot \sqrt[2]{\mu_{ave}}\Delta \frac{dE}{dx}\sqrt{D_{diff} + \frac{u^2 d^2}{192 D_{diff}}}}{E_{ave}\sqrt{\frac{dE}{dx}}} \quad (18)$$

If resolution is set to 1 (complete separation in traditional separations), $\Delta \mu$ becomes $\Delta \mu_{min}$ (the smallest change in mobilities that can be separated with adequate resolution) and is equal to $$\Delta \mu_{min} = \frac{R \cdot \sqrt[2]{\mu_{ave}}\Delta \frac{dE}{dx}\sqrt{D_{diff} + \frac{u^2 d^2}{192 D_{diff}}}}{E_{ave}\sqrt{\frac{dE}{dx}}} \quad (19)$$

3. Discussion

According to this model and theoretical assessment, several factors can influence resolution. Most of this discussion is centered on the finding the minimum difference in electrophoretic mobilities which can be separated because this value can be easily compared to other electrophoretic techniques. The factors which influence resolution are capillary diameter, flow rate, average electrophoretic mobility, and field strength—within the capillary or channel and the difference in field strength between adjoining entrances. All other factors can be derived from these parameters. A good example is capillary diameter. It influences resolution through Taylor-Aris dispersion (eqn. 7) and the steepness of the gradient (dE/dx, approximated by $E_{cap}/d$) at the entrance of the channel.

3.1: Capillary Diameter and Flow Rate

Figure 4:
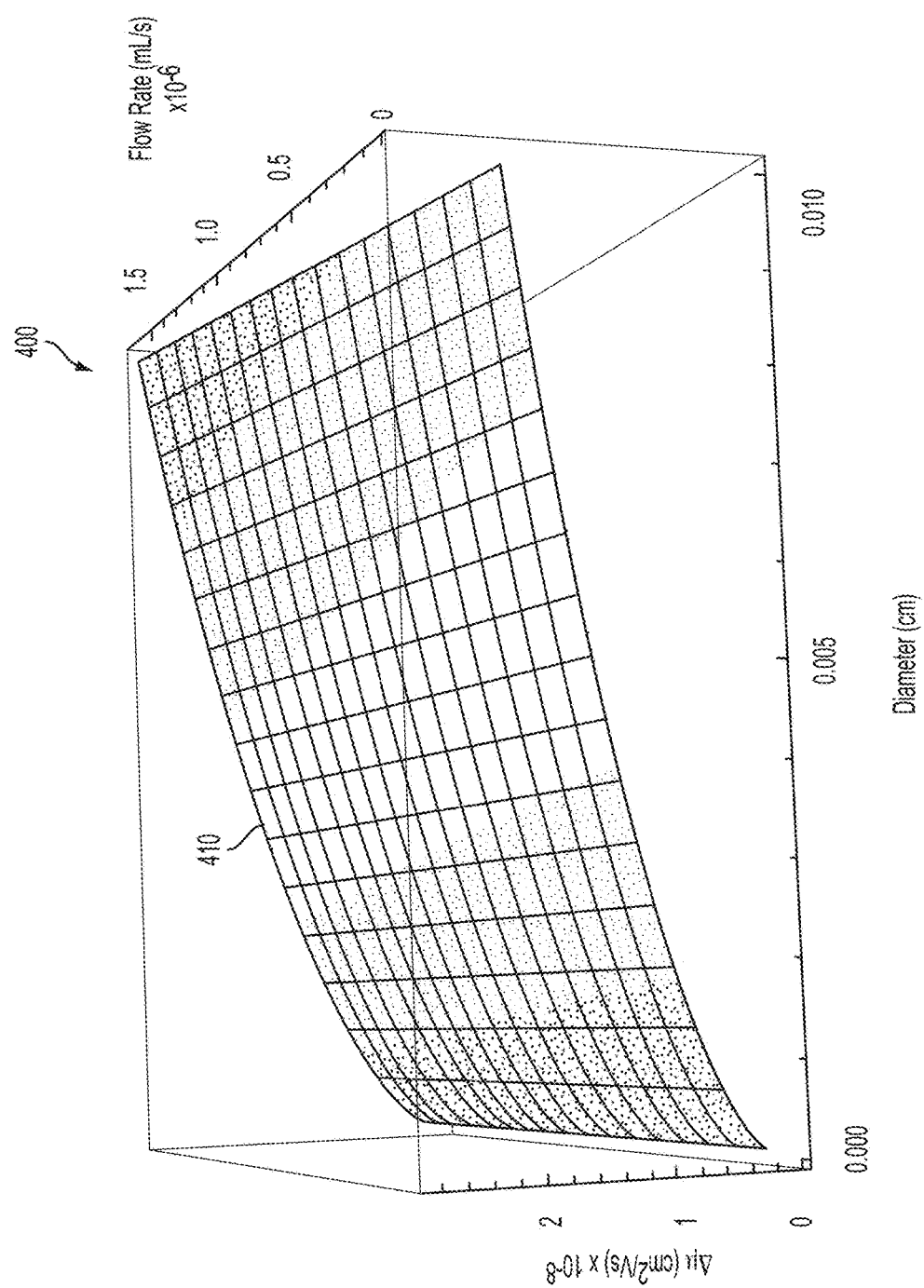
FIG. 4 is a graph 410 of $\Delta\mu$ ((cm$^2$/Vs)×10$^8$) versus diameter (cm) versus flow rate ((mL/s)×10$^{-6}$) in a punctuated-microgradient device, according to some embodiments of the present invention.

Because the relationships between resolution and capillary diameter and flow rate are not algebraically simple (they are not trivial linear, exponential, or logarithmic relationships), they are assessed graphically (FIG. 4). Note that in this assessment, the smaller $\Delta \mu$ is, the better the resolution. Accordingly, resolution is best when the capillary diameter is smaller and flow rate is lower. The strongest effect is a reduction in Taylor-Aris dispersion at small diameters and low flow rates, and an additional effect is an increased gradient at the capillary entrance. Since the smaller diameters positively influence resolution through two mechanisms, increased gradient and reduced dispersion, it dominates the relationship relative to flow. Resolution can be significantly increased by reducing channel diameters—by orders of magnitude, but at the cost of reduced volume flow rate. This is directly offset by the opportunity to operate this strategy with massively parallel interfaces, all with small-diameter, high-resolution interfaces, while attaining the desired bulk fluid transfer.

3.2: Smallest Separable Difference in Electrophoretic Mobilities

According to the calculations presented here, the smallest difference in mobilities of species ($\Delta \mu_{min}$) that can be separated (R=1) is ~$10^{-9}$ cm$^2$/Vs, occurs at the smallest common capillary diameter of 1 µm, a relatively low fluid velocity of 100 µm/s, $\Delta dE/dx$ of 10 V/cm$^2$ (assuming a large diffusion coefficient of 6×$10^{-4}$ cm$^2$/s, and an $\mu_{ave}$ of 5.0× $10^{-5}$ cm$^2$/Vs). Driving these down to obvious limits where assumed physics breakdown (200-nm channel diameter, 3000 V/cm field, 50 µm/s flow velocity) gives ~$10^{-11}$ cm$^2$/Vs for a minimum difference in mobilities that can be distinguished. As a comparison, results were noted from the ultrahigh-voltage CE data produced by Hutterer and Jorgenson in 1999 [30]. According to the data presented in their impressive experimental traditional capillary-zone electrophoresis (CE) study, electrokinetic-mobility differences as small as $10^{-7}$ cm$^2$/Vs were separated at 120 kV total applied field and runs lasted approximately 1 hour. Our theoretical data are comparable to some of the most notable experimental CE data.

3.3: Peak Capacity

Another measure of the quality of a separation process is peak capacity. Peak capacity is defined as the amount (number) of distinguishable peaks, or elements, that can be separated in a given space or time. Peak capacity is a valuable separations metric because it accounts for the total amount (number) of differentiable elements, as opposed to just comparing between two species as in resolution. In electrophoretic exclusion, peak capacity is the total number of species that can be differentiated in individual reservoirs, assuming R=1.

The calculated peak width (2σ) varies across the experimental space. To account for this variation, $\Delta \mu$ was calculated at both the lowest reasonable electrophoretic mobility and the highest for an otherwise constant system. To calculate this theoretical peak capacity ($n_c$), several assumptions were made. First, it was determined that the range of electric fields that could successfully be used for separation were between 10 and 1000 V/cm. A channel diameter of 1 µm was assumed and the $\Delta dE/dx$ between entrances was 10 V/cm$^2$. Diffusion (D) was set at 6×$10^{-4}$ cm$^2$/s, and hydrodynamic velocity ranged between 0.1 and 1 mm/s. Next, the smallest $\mu_{ave}$ (referred to as $\mu_{min}$) was calculated using the lowest linear velocity and the largest electric field strength to be $\Delta \mu_{min} = 10^{-5}$ cm$^2$/Vs. The largest $\mu_{ave}$ (referred to as $\mu_{max}$)

was determined by using the highest linear velocity divided by the lowest electric field $\Delta\mu_{max}=10^{-2}$ cm$^2$/Vs.

The smallest separable difference in mobilities between species at R=1, $\Delta\mu_{min}$, was calculated at both the $\mu_{min}$ and $\mu_{max}$ that was defined above. For $\Delta\mu_{min}$ at $\mu_{min}$, $\Delta\mu_{min}$ was calculated using eqn. 18, which resulted in:

$$\Delta\mu_{min_{\mu min}}=10^{-10} \text{ cm}^2 \text{/Vs} \quad (20)$$

Similarly, $\Delta\mu_{min}$ at $\mu_{max}$ was calculated, except the smallest electric field (10 V/cm) was used for $E_{ave}$, the largest flow velocity (1 mm/s) was used, and dE/dx was calculated as $1.0\times10^{-5}$ V/cm$^2$:

$$\Delta\mu_{min_{\mu max}}=10^{-5} \text{ cm}^2\text{/Vs} \quad (21)$$

Finally, the total peak capacity $n_c$ (number of species that can be differentiated in individual reservoirs) was calculated by using the range of mobilities divided by the average $\Delta\mu_{min}$:

$$n_c = \frac{\mu_{max} - \mu_{min}}{\Delta\mu_{min_{\mu max}} + \Delta\mu_{min_{\mu max}}/(2)} = 1200 \quad (22)$$

These calculations indicate that electrophoretic exclusion can be used for the isolation of analytes in samples that contain a large number of species and whose species cover a large range of mobilities. A similar technique, electric-field-gradient focusing, suggested peak capacities of over 10,000 could be achieved [17], while capillary isoelectric focusing reported an experimental peak capacity of over 4000 [31].

Although the peak capacity for the electrophoretic exclusion of the present invention is already comparable to some of the better one-dimensional separation techniques, some embodiments are further improved by stacking separation steps, while varying the buffer pH, ionic strength, etc. (moving the effluent from a single element, changing the buffer and separating on a new element), which changes the electrophoretic mobilities of the species and allows them to be isolated in different locations. Electrophoretic exclusion is a dynamic technique that allows for adjustments to further improve its separation efficiency.

FIG. 5A is a schematic diagram of a serial electrophoretic exclusion device 501, according to some embodiments of the present invention. In some embodiments, a series of reservoirs, 1341, 1342, 1343 . . . 134n, are connected in series using a plurality of electrode capillaries 130, each having an electrode tip 143. A pressure differential is introduced between the left-most source reservoir 1341 and the right-most destination reservoir 134n (e.g., in some embodiments, using a pump 520 (e.g., an electrokinetic pump such as electro-osmosis pump, pneumatic pump, hydrodynamic pump or the like)), in order to urge a fluid flow from left to right relative to FIG. 5A, successively through reservoirs 1342, 1343, and other optional serially connected reservoirs. In some embodiments, a plurality of target-species removal tubes or capillaries 530 are provided, such that the target species collected and concentrated in each reservoir can be individually removed for use or further processing. In some embodiments such as shown in FIG. 5A, each successive capillary is fabricated to have a different length (e.g., in some embodiments, successively smaller lengths X as one moves left to right), in order to induce different successively greater $\Delta$dE/dx for the successive capillaries 530 in the chain. In other embodiments, the capillary lengths are made the same, but different voltages are applied for V1, V2, V3, . . . Vn, in order to provide different (e.g., in some embodiments, successively smaller) $\Delta$dE/dx for the successive capillaries as the fluid moves left-to-right. In still other embodiments, both the capillary length and the applied voltages are varied. In some embodiments, a single voltage supply is used and a resistor voltage divider are used together to provide the different voltages at the tips of the successive capillaries. In some embodiments, the capillaries themselves form a resistive voltage divider, and a single voltage supply is connected between the right-most electrode 141 and the left-most capillary-tip electrode 143 (without using an external voltage divider), and each capillary is fabricated with a different length and/or different diameter (or cross-sectional area), in order to provide different $\Delta$dE/dx for the successive capillaries.

For example, the left-most first capillary 130, which extends between reservoir 1341 and reservoir 1342, would be configured to have the largest $\Delta$dE/dx. A first species, the species with the greatest electrophoretic mobility, will be excluded by the left-most capillary 130 that extends between reservoir 1341 and reservoir 1342 (because its electrophoretic velocity (for the given $\Delta$dE/dx of that capillary) toward the left exceeds the fluid velocity toward the right), while other species of interest will pass through that capillary 130, thus isolating the first species in reservoir 1341 and passing the others into reservoir 1342. The second capillary 130 that extends between reservoir 1342 and 1343 would be configured to have the next-largest $\Delta$dE/dx. A second species, the species with the next-greatest electrophoretic mobility, will be excluded by the capillary 130 that extends between reservoir 1342 and reservoir 1343 (because its electrophoretic velocity (for the given $\Delta$dE/dx of that capillary) toward the left exceeds the fluid velocity toward the right), while other species of interest will pass through that second capillary 130, thus isolating the second species in reservoir 1342 and passing the others into reservoir 1343. This process is then repeated through as many successive reservoirs and capillaries as desired (in some embodiments, hundreds or thousands or tens of thousands or hundreds of thousands of successive reservoirs and capillaries are used). In some embodiments, the isolated species of interest are removed using individual capillaries or passages 530. In other embodiments, the isolated species are analyzed in the reservoirs into which they were separated using light (e.g., transmitted, reflected, or fluoresced, etc.), electrical conductivity, photo-micrography, or other suitable means. In some embodiments, once a separation into the plurality of chambers is performed using a first solvent or carrier fluid, that first solvent or carrier fluid is flushed through the system and replaced by a second different solvent or carrier fluid, and additional separations are performed to further separate and isolate species that may not have been capable of separation using the first solvent, and this process of iterative separations using different solvents or carrier fluids is repeated as needed.

FIG. 5B is a schematic diagram of one stage of a parallel electrophoretic exclusion device 502, according to some embodiments of the present invention. In some embodiments, parallel electrophoretic exclusion device 502 provides the same $\Delta$dE/dx on each of a plurality of capillaries 130 that run in parallel between reservoir 1341 and reservoir 1342 (i.e., each of the plurality of capillaries 130 in FIG. 5B start in reservoir 1341 and end in reservoir 1342), in order to increase the volume of material that is separated in a given amount of time.

FIG. 5C is a schematic diagram of a parallel-and-serial electrophoretic exclusion device 502, according to some embodiments of the present invention. In some embodiments, parallel electrophoretic exclusion device 503 provides the same ΔdE/dx on each of a plurality of capillaries 130 that run in parallel between reservoir 1341 and reservoir 1342 (i.e., each of the left-most plurality of capillaries 130 in FIG. 5C start in reservoir 1341 and end in reservoir 1342), in order to increase the volume of material that is separated in a given amount of time, and a plurality of such parallel separations are performed serially, in order to isolate greater quantities of each of the different species. In various embodiments, the ΔdE/dx values of the various stages are varied as described above for FIG. 5A.

Figure 5D:
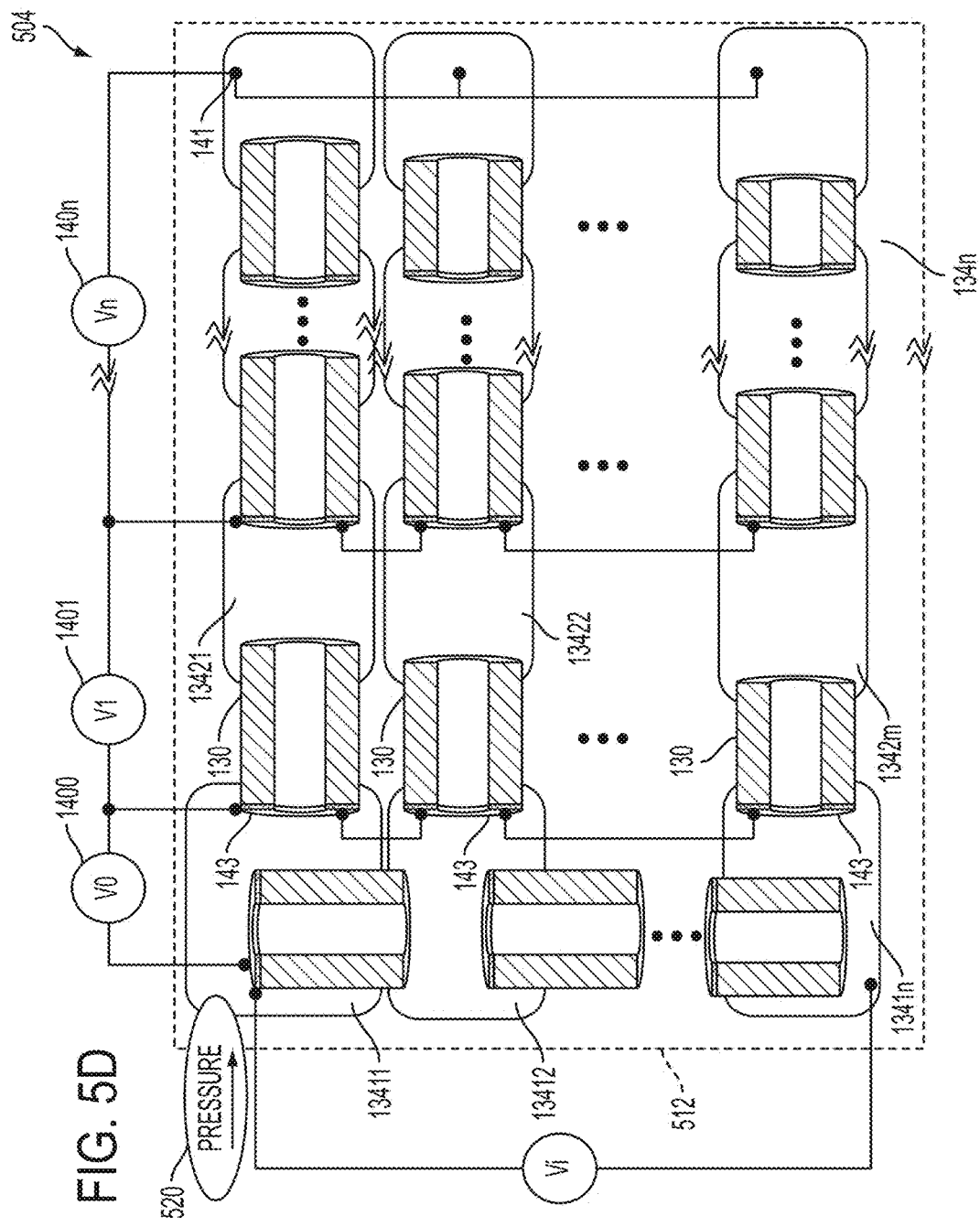
FIG. 5D is a schematic diagram of an electrophoretic exclusion device 504, according to some embodiments of the present invention.
Figure 7:
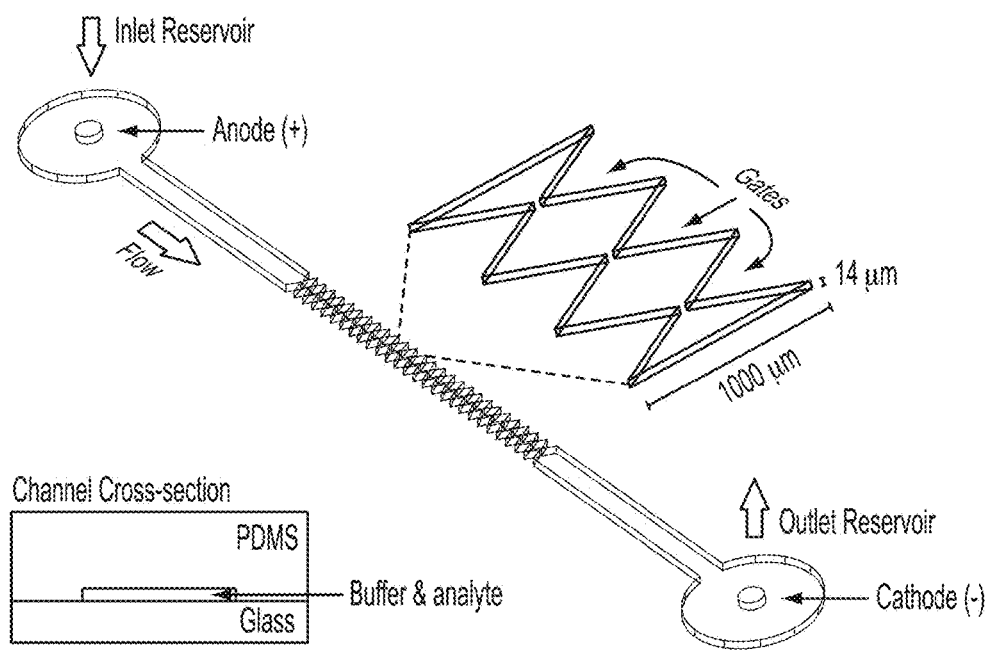
FIG. 7 is a schematic diagram of a g-iDEP microchannel. For these experiments, devices were constructed of glass and PDMS.
Figures 8A, 8B, 8C:
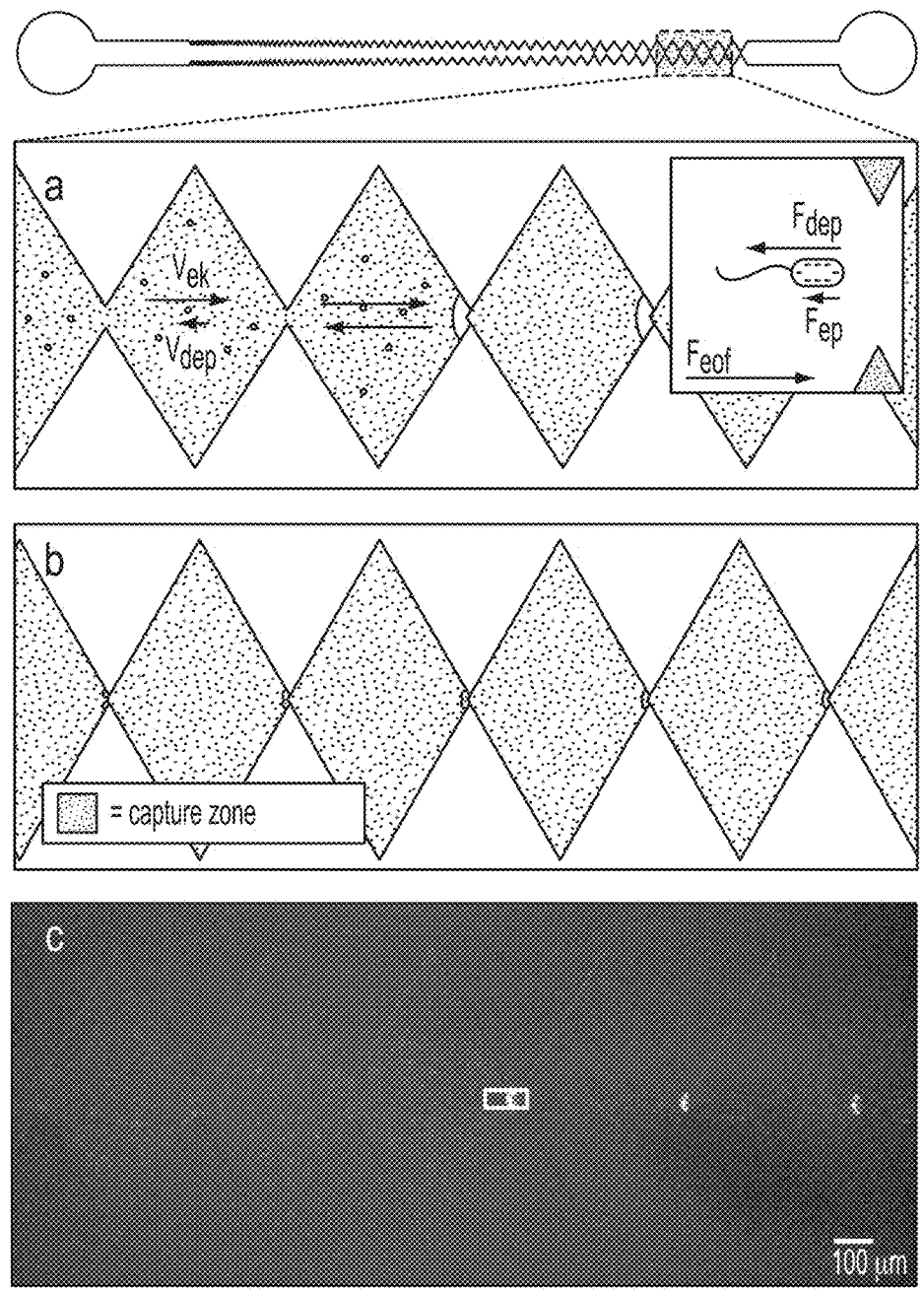
FIGS. 8A-8C. (a) Illustration showing capture of *E. coli* organisms as predicted by the presence of opposing electrokinetic and dielectrophoretic forces. (b) Capture zones modeled using COMSOL Multiphysics. (c) Image showing capture of fluorescently-labeled bacteria. The yellow box indicates the region of interest used for fluorescence intensity measurement.
Figure 9:
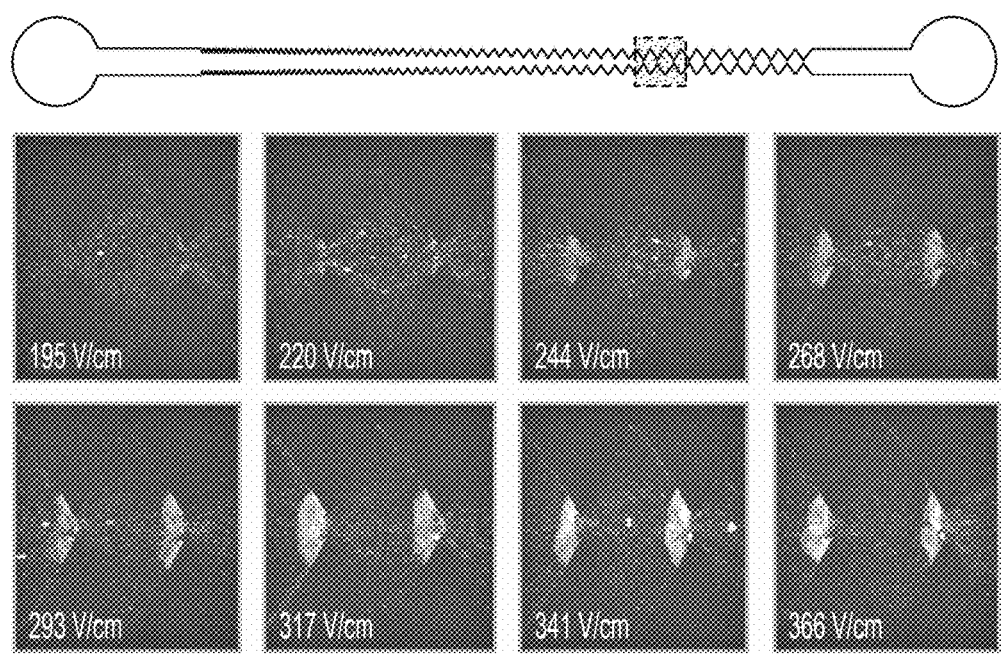
FIG. 9 illustrates capture of O6:K1:H1 at 90-μm gates. In each image, $t_{app}$=5 seconds. Capture only occurs above a threshold value of $E_{app}$.
Figures 10A, 10B:
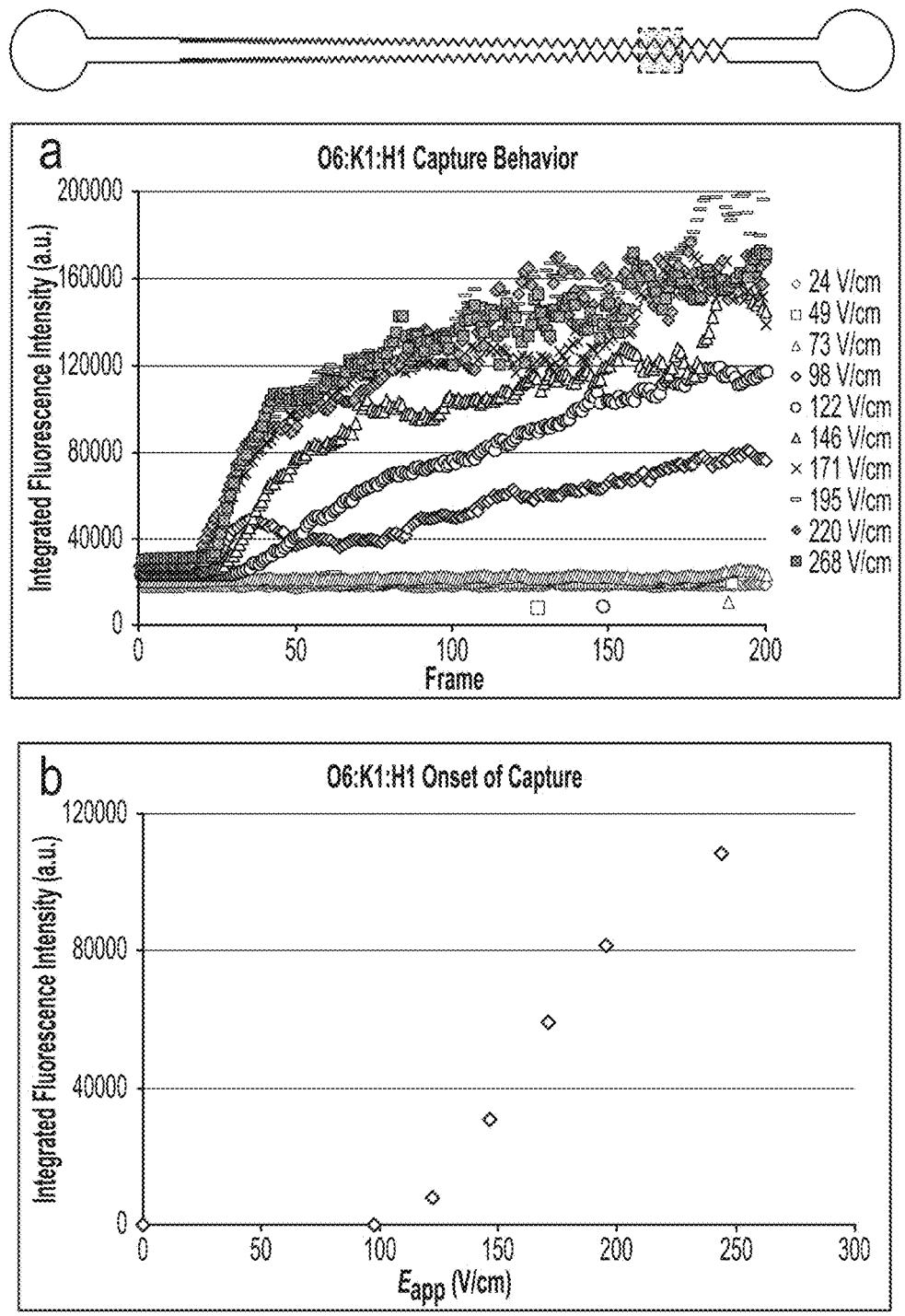
FIGS. 10A and 10B. Plots showing fluorescence intensity data for capture of O6:K1:H1. (a) Plot showing the accumulation of material over time for various applied field strengths. No capture occurs when $E_{app}$ is 100 V/cm or less, even over extended periods of time. Above this range, capture is observed almost immediately. 120 to 200 V/cm comprise a transition zone, where capture begins to occur, but is not completely exclusive. Above 200 V/cm, increasing the applied field strength does not appreciably affect the accumulation of material with time. (b) Plot showing fluorescence intensity increase at a capture zone (gate) versus applied field strength. Each FI measurement was taken after 5 seconds of applied potential.
Figure 11:
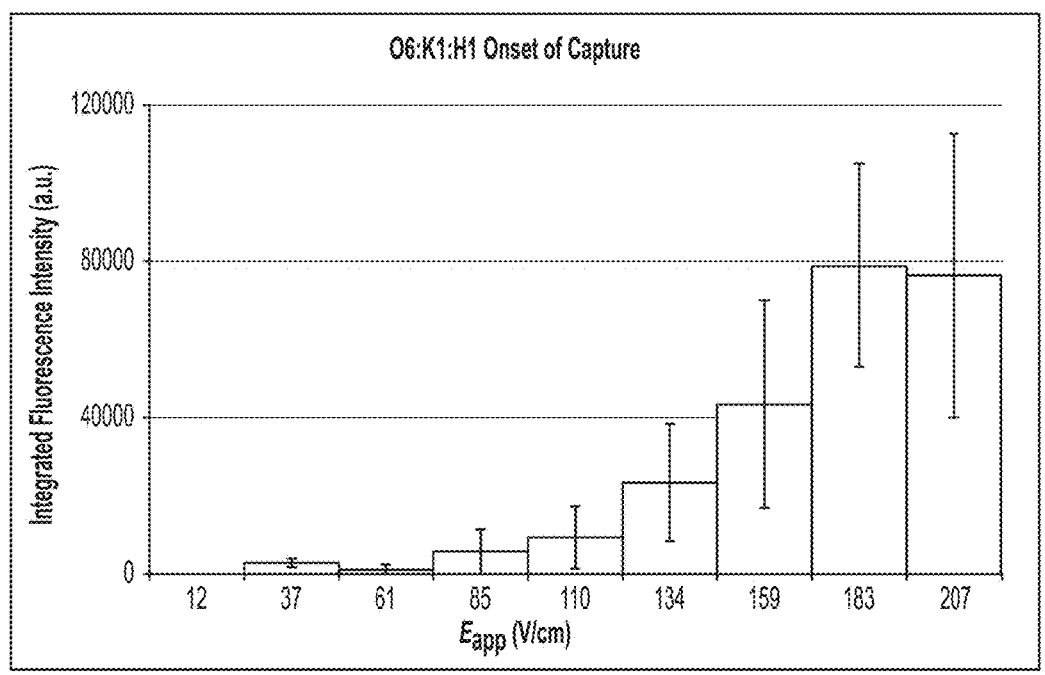
FIG. 11 is a plot showing FI intensity versus applied field strength for five different preparations of serotype O6:K1:H1, each captured on a separate device.
Figure 12:
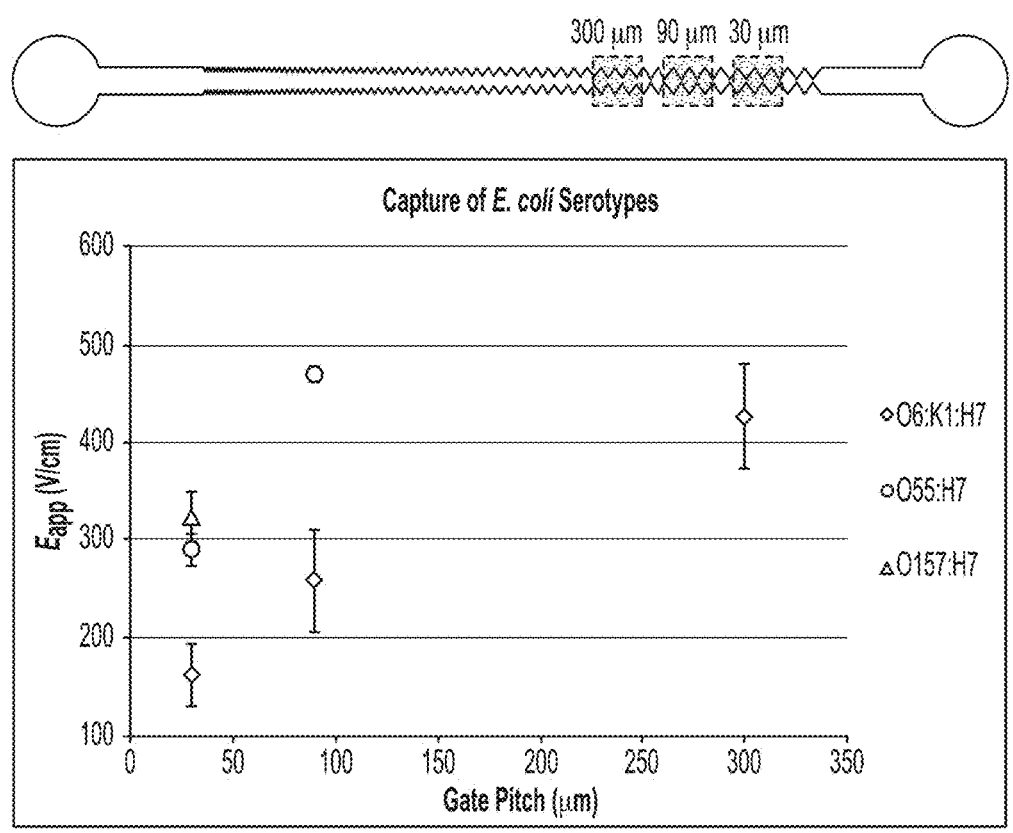
FIG. 12 is a plot showing onset field required for capture for all three serotypes of *E. coli*, at three different gate pitches (27, 90, and 300 μm). Onset field differs for all three serotypes, indicating that they can be differentiated based on their electrokinetic behavior within a g-iDEP device. The data marker hides error bars for O55:H7 at the 90-μm gates.

FIG. 5D is a schematic diagram of an electrophoretic exclusion device 504, according to some embodiments of the present invention. In some embodiments, electrophoretic exclusion device 504 provides different ΔdE/dx on each of a plurality of capillaries 130 that run in parallel between reservoirs 13411, 13412, ... 1341n (with fluid flowing successively from reservoir 13411 to reservoir 13412, ... to reservoir 1341n, and performing a first separation. In some embodiments, electrophoretic exclusion device 504 provides different ΔdE/dx on each of a plurality of capillaries 130 that run in parallel between reservoirs 13411, 13412, ... 1341n and reservoirs 13421, 13422, ... 1342n (i.e., each of the left-most plurality of capillaries 130 in FIG. 5C that start in reservoirs 13411, 13412, ... 1341n respectively and end in different reservoirs 13421, 13422, ... 1342n respectively), in order to increase the number of materials that are separated in a given amount of time, and a plurality of such parallel separations are performed serially, in order to isolate greater numbers of the different species. In various embodiments, the ΔdE/dx values of the various stages are varied as described above for FIG. 5A.

References cited in Example 1:
1. Ricker, R.D. and L.A. Sandoval, *Fast, reproducible size-exclusion chromatography of biological macromolecules*. J. Chromatogr. A, 1996. 743(1): p. 43-50.
2. Kanner, S.B., A.B. Reynolds, and J.T. Parsons, *IMMUNOAFFINITY PURIFICATION OF TYROSINE-PHOSPHORYLATED CELLULAR PROTEINS*. J. Immunol. Methods, 1989. 120(1): p. 115-124.
3. Giddings, J.C. and K. Dahlgren, *Resolution and peak capacity in equilbrium-gradient methods of separation*. Sep. Sci., 1971. 6(3): p. 345-&.
4. Cong, Y.Z., et al., *Improved protein separation by microchip isoelectric focusing with stepwise gradient of electric field strength*. J. Sep. Sci., 2009. 32(3): p. 462-465.
5. Cui, H.C., et al., *Multistage isoelectric focusing in a polymeric microfluidic chip*. Anal. Chem., 2005. 77(24): p. 7878-7886.
6. Hofmann, O., et al., *Adaptation of capillary isoelectric focusing to microchannels on a glass chip*. Anal. Chem., 1999. 71(3): p. 678-686.
7. Greenlee, R.D. and C.F. Ivory, *Protein focusing in a conductivity gradient*. Biotechnology Progress, 1998. 14(2): p. 300-309.
8. Ross, D. and L.E. Locascio, *Microfluidic temperature gradient focusing*. Analytical Chemistry, 2002. 74(11): p. 2556-2564.
9. Kelly, R.T. and A.T. Woolley, *Electric field gradient focusing*. Journal of Separation Science, 2005. 28(15): p. 1985-1993.
10. Shackman, J.G. and D. Ross, *Counter-flow gradient electrofocusing*. Electrophoresis, 2007. 28(4): p. 556-571.
11. Danger, G. and D. Ross, Development of a temperature gradient focusing method for in situ extraterrestrial biomarker analysis. Electrophoresis, 2008. 29(15): p. 3107-3114.
12. Burke, J.M. and C.F. Ivory, Influence of the semipermeable membrane on the performance of dynamic field gradient focusing. Electrophoresis, 2010. 31(5): p. 893-901.
13. Huang, Z. and C.F. Ivory, *Digitally controlled electrophoretic focusing*. Anal. Chem., 1999. 71(8): p. 1628-1632.
14. Giddings, J.C., *Coiled columns and resolution in gas chromatography*. J. Chromatogr., 1960. 3(6): p. 520-523.
15. Giddings, J.C., *Liquid chromatography with operating conditions analogous to those of gas chromatography*. Anal. Chem., 1963. 35(13): p. 2215-&.
16. Foret, F., M. Deml, and P. Bocek, CAPILLARY ZONE ELECTROPHORESIS—QUANTITATIVE STUDY OF THE EFFECTS OF SOME DISPERSIVE PROCESSES ON THE SEPARATION EFFICIENCY. Journal of Chromatography, 1988. 452: p. 601-613.
17. Tolley, H.D., et al., Equilibrium gradient methods with nonlinear field intensity gradient: A theoretical approach. Anal. Chem., 2002. 74(17): p. 4456-4463.
18. Shackman, J.G., M.S. Munson, and D. Ross, Gradient elution moving boundary electrophoresis for high-throughput multiplexed microfluidic devices. Anal. Chem., 2007. 79(2): p. 565-571.
19. Ross, D. and J.G. Kralj, Simple Device for Multiplexed Electrophoretic Separations Using Gradient Elution Moving Boundary Electrophoresis with Channel Current Detection. Anal. Chem., 2008. 80(24): p. 9467-9474.
20. Ross, D. and E.F. Romantseva, Gradient Elution Moving Boundary Electrophoresis with Channel Current Detection. Anal. Chem., 2009. 81(17): p. 7326-7335.
21. Ross, D., Step width, spacing, and resolution in gradient elution moving boundary electrophoresis. Part 1. Theory and comparison with zone electrophoresis. Electrophoresis, 2010. 31(22): p. 3650-3657.
22. Polson, N.A., D.P. Savin, and M.A. Hayes, Electrophoretic focusing preconcentration technique using a continuous buffer system for capillary electrophoresis. J. Microcolumn Sep., 2000. 12(2): p. 98-106.
23. Meighan, M.M., et al., Electrophoretic exclusion for the selective transport of small molecules. Electrophoresis, 2009. 30(21): p. 3786-3792.
24. Meighan, M.M., et al., Investigation of Electrophoretic Exclusion Method for the Concentration and Differentiation of Proteins. Anal. Chem., 2011. 83(1): p. 368-373.
25. Keebaugh, M.W., P. Mahanti, and M.A. Hayes, Quantitative assessment of flow and electric fields for electrophoretic focusing at a converging channel entrance with interfacial electrode. Electrophoresis, 2012. 33(13): p. 1924-1930.
26. Kenyon, S.M., N.G. Weiss, and M.A. Hayes, Using electrophoretic exclusion to manipulate small molecules and particles on a microdevice. Electrophoresis, 2012. 33(8): p. 1227-1235.
27. Pacheco, J.R., K.P. Chen, and M.A. Hayes, A study on the condition for differential electrophoretic transport at a channel entrance. Electrophoresis, 2007. 28(7): p. 1027-1035.
28. Giddings, J.C., *Basic approaches to separation—steady-state zone and layers*. Sep. Sci. Technol., 1979. 14(10): p. 871-882.

29. Taylor, G., DISPERSION OF SOLUBLE MATTER IN SOLVENT FLOWING SLOWLY THROUGH A TUBE. Proc. R. Soc. London A, 1953. 219(1137): p. 186-203.
30. flutterer, K.M. and J.W. Jorgenson, *Ultrahigh-voltage capillary zone electrophoresis*. Anal. Chem., 1999. 71(7): p. 1293-1297.
31. Shen, Y.F., S.J. Berger, and R.D. Smith, *Capillary isoelectric focusing of yeast cells*. Anal. Chem., 2000. 72(19): p. 4603-4607.

EXAMPLE 2

Since the first humans smelted copper ore, the separation of materials in time and space has played a central role in technological progress. The ability to manipulate matter and cause its selective movement has, at the root, enabled the development of modern science. Early scientists concerned themselves with the isolation and identification of elements and compounds. In more recent centuries and decades, the selective capture, concentration, or manipulation of bioparticles has become increasingly significant. Quick and effective control of the transport of biological material lies at the heart of many medical, pharmaceutical, and environmental technologies. Many existing methodologies, such as those used in clinical diagnosis, leave room for improvement. Development of new bioanalytical separatory tools will also continue to drive scientific and medical innovation.

In many analytical separations, components become segregated as they move along a separatory axis at different rates. Chromatography, electrophoresis, and sedimentation serve as examples of this paradigm. Such methods are often plagued by band-broadening and dispersive effects, which decrease analyte concentration throughout the process. This can present difficulties with subsequent detection or multi-dimensional analysis. Steady-state separation schemes, such as equilibrium-gradient techniques, employ competing forces to concentrate and fractionate analytes simultaneously. Isoelectric focusing, isopycnic sedimentation, and electric-field-gradient focusing serve as paradigmatic examples. It is important to note that within the context of separation science the term "gradient" refers to any force that varies along an axis. This term is not necessarily used to describe field nonlinearity.

The present invention improves on a relatively new variant of equilibrium-gradient separation, which utilizes a combination of dielectrophoresis (DEP), electrophoresis (EP), and electro-osmotic flow (EOF). This method, first reported in 2007, is an extension of insulator-based DEP techniques called direct-current insulator-based gradient-dielectrophoresis (DC-iGDEP). This technique utilizes a continuous microchannel patterned with sequential, constrictive insulating features. These constrictions, termed "constricted passageways" or "gates" hereafter, create a series of DEP-inducing electric-field non-uniformities. As a result of the geometry of the channel, increasingly strong DEP forces are induced along the channel. Particles traveling through the microchannel are propelled by a combination of electrophoresis (EP) and electro-osmosis (EO). Since DEP forces scale differently with the channel's cross-sectional area than do EP and EO, unique "traps" are formed at each gate as the gates become sequentially narrower. This causes physicochemically distinct particles to settle into discrete zones near different gates, assuming unique positions along the channel's separatory axis based on their electrophoretic and dielectrophoretic mobilities.

The use of electric-field microgradients for purely electrokinetic equilibrium-gradient separation allows for a high degree of analyte selectivity. Considered together, a particle's electrophoretic and dielectrophoretic mobilities represent an array of properties including size, charge, polarizability, shape, and heterogeneity. Interrogating all these properties together yields a separatory scheme that can be fine-tuned for high-resolution capture and concentration of analytes.

Theory

Particle motion within a direct-current insulator-based gradient-dielectrophoresis (DC-iGDEP) channel results from a superposition of forces induced by the applied electric field. These forces vary predictably with the applied electric field, and depend on electro-physical properties of the analyte. As such, a particle's response to a given electric field is described by electrokinetic mobilities intrinsic to the particle. Two of the chief electrokinetic forces acting upon particles are electrophoresis and electroosmotic flow. The former acts directly upon the particle, while the latter causes viscous drag on suspended particles due to bulk flow. Electrophoretic and electroosmotic forces are both proportional and vectorially identical to the applied electric field. As a result, treatments of this topic generally combine these two terms into a single electrokinetic mobility ($\mu_{EK}$). The third electrokinetic force to consider is dielectrophoresis, which can differ from the other forces in both magnitude and direction. A given particle's dielectrophoretic response is characterized by its dielectrophoretic mobility ($\mu_{DEP}$).

Definitions

For this discussion, two arbitrarily similar particles will be considered, each with distinct electrokinetic mobility ($\mu_{EK1}$ and $\mu_{EK2}$) and dielectrophoretic mobility ($\mu_{DEP1}$ and $\mu_{DEP2}$). To achieve separation of two particles, their mobility ratios must differ in some way. The ratio of the mobilities ($\mu_{EK}/\mu_{DEP}$) diverges if they possess differing values for either $\mu_{EP}$ or $\mu_{DEP}$. Any such difference is a requirement for separation:

$$\frac{\mu_{EK1}}{\mu_{DEP1}} \neq \frac{\mu_{EK2}}{\mu_{DEP2}}. \tag{23}$$

Within the DC-iGDEP device, the shape of the channel wall creates a series of strictures in the cross-sectional area of the channel. The wall's point of closest approach to one another (hereafter referred to as a gate) induces a local maximum in the electric field. For any two arbitrary neighboring gates, the local maxima are defined as $E_1$ and $E_2$. The average of these two local maxima is $E_{ave}$.

Near or at these gates, the applied electric field changes intensity. The local field gradient is a key element and is defined as the maximum local change in electric-field strength near the entrance to a gate. The second important descriptor of field properties in the channel is the global field gradient. The global field gradient is defined as the difference in the local field gradients at neighboring gates, divided by the distance between the two features:

$$\text{Local field gradient } \left(\frac{dE}{dx}\right)_{local} = \text{local maximum, and} \tag{24}$$

$$\text{Global field gradient } \left(\frac{dE}{dx}\right)_{global} = \frac{\left(\frac{dE}{dx}\right)_{local} - \left(\frac{dE}{dx_1}\right)_{local}}{\Delta x}. \tag{25}$$

The degree of nonuniformity in the electric field is similarly significant to dielectrophoretic separations. It is encapsulated within the DEP force-related term, $\nabla|E|^2$. The maximum local change in this function is the local $\nabla|E|^2$ gradient, and roughly coincides with that of the local electric-field gradient (noting that the maximum field strength near the gate does not occupy the same spatial location). The global $\nabla|E|^2$ gradient is defined as the difference in the local maxima of the function $\nabla|E|^2$ near neighboring gates, divided by the distance between the two:

$$\text{Local } \nabla|E|^2 \text{ gradient: } \left(\frac{d\nabla|E|^2}{dx}\right) = \text{local maximum} \quad (26)$$

and $$\text{Global } \nabla|E|^2 \text{ gradient: } \left(\frac{d\nabla|E|^2}{dx}\right)_{global} = \frac{\left(\frac{d\nabla|E|^2}{dx_2}\right)_{local} - \left(\frac{d\nabla|E|^2}{dx_1}\right)_{local}}{\Delta x}. \quad (27)$$

Resolution (R) is defined as the selective capture of each species at nearest neighbor gates. This discussion will center on the classical definition of resolution used in separation science, where $\Delta X$ is the distance between the maxima of two capture zones and $\sigma$ is the standard deviation of a peak. Resolution, so defined, has long been used as an indicator in analytical separations. It specifies the degree of separation or overlap between two analytes in a separations scheme.

$$R = \frac{\Delta X}{4\sigma} \quad (28)$$

This approach utilizes local electric-field microgradients (E and $\nabla|E|^2$) to form multiple, distinct capture zones. These local gradients vary sequentially with gate number along the channel's longitudinal axis, giving rise to corresponding global gradients. The location of capture depends on a species' $\mu_{EK}/\mu_{DEP}$ ratio. $\Delta X$ can be defined in terms of particle properties that yield separation along the global gradient. As a result, the net velocity of each species (as it relates to electric field properties) and the global gradients between gates become the most important factors in describing resolution. The velocity components resulting from electrokinetic forces are outlined below, where $$\overline{\mu} = \frac{(\mu_1 - \mu_2)}{2} \quad (29)$$

for two closely related target analytes (EK and DEP subscripts omitted).

$$v_{EK_1} = \mu_{EK_1} E \quad (30)$$

$$v_{DEP_1} = \mu_{DEP_1} \nabla|E|^2 \quad (31)$$

$$v_{EK_2} = \mu_{EK_2} E \quad (32)$$

$$v_{DEP_2} = \mu_{DEP_2} \nabla|E|^2 \quad (33)$$

$$\overline{v}_{EK} = \overline{\mu}_{EK} E \quad (34)$$

$$\overline{v}_{DEP} = \overline{\mu}_{DEP} \nabla|E|^2 \quad (35)$$

Note that the global gradients depend on the geometry of the sequence of insulating structures. Both the height (or aperture) of the gates and the horizontal spacing between gates figure significantly into the nature of these gradients. The practical extents of channel geometry are governed by other physical limitations, but are not significant to this discussion.

Since particle trapping requires v=0 for the particles to be trapped, the location of capture zone formation depends on net particle velocity:

$$\text{where: } \Delta X = \frac{\Delta v}{\frac{dv}{dx}} \quad (36)$$

$$\Delta v = \Delta \mu_{EK} E_{ave} + \Delta \mu_{DEP} \nabla|E|^2_{ave} \quad (37)$$

$$\frac{dv}{dx} = \overline{\mu}_{EK} \Delta\left(\frac{dE}{dx}\right) + \overline{\mu}_{DEP} \Delta\left(\frac{d\nabla|E|^2}{dx}\right) \quad (38)$$

Thus, the overall distance between peak centroids within a sawtooth channel is:

$$\Delta X = \frac{\Delta \mu_{EK} E_{ave} + \Delta \mu_{DEP} \nabla|E|^2_{ave}}{\overline{\mu}_{EK} \Delta\left(\frac{dE}{dx}\right) + \overline{\mu}_{DEP} \Delta\left(\frac{d\nabla|E|^2}{dx}\right)} \quad (39)$$

Peak width within this system is governed by two competing types of force: those that focus the analyte particles, and those that cause dispersion. Focusing forces in this system result from opposing microgradients in the electric-field profile. Specifically, these are $(dE/dX)_{local}$ and $(d\nabla|E|^2/dx)_{local}$ near a gate. For capture to occur, the two forces must oppose each other. For small displacements from the balance point, a particle will experience a force and resultant velocity directed back towards that point.

FIG. 6A is a schematic diagram of a serial electrophoretic and dielectrophoretic exclusion device 601, according to some embodiments of the present invention. In some embodiments, a continuous microchannel 621 is formed in the substrate 611. In some embodiments, a pressure is applied by a pump 620 that urges a flow of material (e.g., a fluid that includes a plurality of species in a solvent) from left to right (in relation to the drawing) through microchannel 621. In some embodiments, continuous microchannel 621 is shaped to form a sequential plurality of constrictive passageways 630$_1$ ... 630$_N$, wherein constrictive passageway 630$_1$ connects reservoir 6341 to reservoir 6342, constrictive passageway 630$_2$ connects reservoir 6342 to reservoir 6343, and so on until constrictive passageway 630$_N$ connects to the last reservoir 634N. Reference 630 refers generally to each of the constrictive passageways 630$_1$ ... 630$_2$. In some embodiments, the aperture 1 of constrictive passageway 630$_1$ is larger in cross-sectional area than aperture 2 of constrictive passageway 630$_2$, and the aperture 2 of constrictive passageway 630$_2$ is larger in cross-sectional area than aperture 3 of constrictive passageway 630$_3$. In some embodiments, the lengths of each of the successive constrictive passageways 630 are different from one another. In some embodiments, the geometric shapes of each of the successive constrictive passageways 630 are different from one another. In some embodiments, an electrical power supply 640 applies a voltage across the microchannel 621, and the various differences in the successive constrictive passageways 630 act to form different electrical fields and dielectric gradients, in order to separate the various species in the material that flows through microchannel 621. Some embodiments include structures (such as capillary passageways similar to capillaries 530 of FIG. 5A) for removing and/or examining the species that are concentrated at the fluid-flow entry (left-hand end in the drawing) or exit (right-hand end in the drawing) of each of a plurality of the successive constrictive passageways 630.

FIG. 6B is a schematic diagram of a saw-tooth-channel electrophoretic and dielectrophoretic exclusion device 602, according to some embodiments of the present invention. In some embodiments, a continuous microchannel 622 having a saw-tooth shaped cross-sectional area is formed in the substrate 612. In some embodiments, a pressure is applied by a pump 620 that urges a flow of material (e.g., a fluid that includes a plurality of species in a solvent) from left to right (in relation to the drawing) through microchannel 622. In some embodiments, continuous microchannel 622 is shaped to form a sequential plurality of constrictive passageways $650_1$ . . . $650_N$, wherein constrictive passageway $650_1$ connects reservoir 6361 to reservoir 6362, constrictive passageway $650_2$ connects reservoir 6362 to reservoir 6363, and so on until constrictive passageway $650_N$ connects to the last reservoir 636N. In some embodiments, the aperture 1 of constrictive passageway $650_1$ is larger in cross-sectional area than aperture 2 of constrictive passageway $650_2$, and the aperture 2 of constrictive passageway $650_2$ is larger in cross-sectional area than aperture 3 of constrictive passageway $650_3$. Reference 650 refers generally to each of the constrictive passageways $650_1$ . . . $650_2$. In some embodiments, the lengths of each of the successive constrictive passageways 650 are different from one another. In some embodiments, the geometric shapes (e.g., the slopes of the walls) of each of the successive constrictive passageways 650 are different from one another. In some embodiments, an electrical power supply 640 applies a voltage across the microchannel 622, and the various differences in the successive constrictive passageways 650 act to form different electrical fields and dielectric gradients, in order to separate the various species in the material that flows through microchannel 622. Some embodiments include structures (such as capillary passageways similar to capillaries 530 of FIG. 5A) for removing and/or examining the species that are concentrated at the entry (left-hand end in the drawing) or exit (right-hand end in the drawing) of each of a plurality of the successive constrictive passageways 650.

Transport (U) in this system can be written in the following form, since it varies with x:

$$U = -ax \quad (40)$$

The slope a represents the intensity of the focusing effects. It is generally linearizable (either by assumptions or using the first non-zero factor in a Taylor-series expansion). Over small distances, the velocity is proportional to the amount of displacement from the balance point. As a result, particles will seek out that location and form a steady-state Gaussian distribution around this point.

The change in velocity (a) can be written as $$a = \mu_{EK}\left(\frac{dE}{dx}\right) + \mu_{DEP}\left(\frac{d\nabla|E|^2}{dx}\right) \quad (41)$$

Therefore $$U = -\left[\mu_{EK}\left(\frac{dE}{dx}\right) + \mu_{DEP}\left(\frac{d\nabla|E|^2}{dx}\right)\right]x \quad (42)$$

Dispersive forces directly compete with the focusing. Sources of dispersion ($D_{TOT}$) include the effects of diffusion ($D_{diff}$) and potentially other effects (joule heating, flow). This discussion will focus only on $D_{diff}$, noting that other effects can be included in an additive manner. Variance of the steady-state Gaussian concentration profile is defined as the dispersive forces divided by the slope of the restoring forces:

$$\sigma^2 = \frac{D_{TOT}}{a} \quad (43)$$

Thus, an expression representing peak width is:

$$\sigma = \left[\frac{D_{TOT}}{\mu_{EK}\left(\frac{dE}{dx}\right) + \mu_{DEP}\left(\frac{d\nabla|E|^2}{dx}\right)}\right]^{\frac{1}{2}}. \quad (44)$$

Resolution
Resolution may be calculated by incorporating the above expressions for ΔX and combined zone width.

$$R = \frac{\Delta X}{4\sigma} = \frac{\left[\frac{\Delta\mu_{EK}E_{ave} + \Delta\mu_{DEP}\nabla|E|^2_{ave}}{\mu_{EK}\Delta\left(\frac{dE}{dx}\right) + \mu_{DEP}\Delta\left(\frac{d\nabla|E|^2}{dx}\right)}\right]}{4\left[\frac{D_{TOT}}{\mu_{EK}\left(\frac{dE}{dx}\right) + \mu_{DEP}\left(\frac{d\nabla|E|^2}{dx}\right)}\right]^{\frac{1}{2}}} \quad (45)$$

or when rearranged:

$$R = \frac{\left(\begin{array}{c}\Delta\mu_{EK}E_{ave} + \\ \Delta\mu_{DEP}\nabla|E|^2_{ave}\end{array}\right)\left[\mu_{EK}\left(\frac{dE}{dx}\right) + \mu_{DEP}\left(\frac{d\nabla|E|^2}{dx}\right)\right]^{\frac{1}{2}}}{4D_{TOT}^{\frac{1}{2}}\left[\bar{\mu}_{EK}\Delta\left(\frac{dE}{dx}\right) + \bar{\mu}_{DEP}\Delta\left(\frac{d\nabla|E|^2}{dx}\right)\right]} \quad (46)$$

In some embodiments, the present invention provides a punctuated microgradient device that includes a substrate having a first continuous microchannel that is patterned with a plurality of sequential, constrictive insulating features to form a plurality of reservoirs including a first, second and third reservoir, and a plurality of constricted passageways including a first constricted passageway that connects the first reservoir to the second reservoir and a second constricted passageway that connects the second reservoir to the third reservoir, wherein the microchannel has walls that are electrically insulative; and a first electrode and a second electrode both operatively coupled to the first microchannel and configured to establish an electric field E within the microchannel. In some embodiments, the first electrode is operatively coupled to the first reservoir along the length of the first microchannel and the second electrode is operatively coupled to the last reservoir along the length of the first microchannel, and a voltage is applied between the first electrode and the second electrode. In some such embodiments, one or more additional electrodes are operatively coupled to the first microchannel along the length of the first microchannel between the first electrode and the second electrode. In some embodiments, a pump is connected to apply a pressure difference between the first reservoir and the last reservoir of the first microchannel in order to urge a flow of material through the first microchannel, wherein the apparatus is configured to establish different electric fields and/or different dielectrophoretic gradients at each of the plurality of constricted passageways along the first microchannel. In some embodiments, a plurality of microchannels, each substantially the same as the first microchannel, are fabricated in a single substrate.

In some embodiments, a plurality of constricted passageways are formed between each successive pair of reservoirs of the plurality of reservoirs, in order to increase the amount of the species collected and concentrated in each one of the plurality of reservoirs.

In some embodiments, the electrical field E includes a first local electrical field $E_1$ in the first constricted passageway and a second local electrical field $E_2$ in the second constricted passageway, and wherein a magnitude of the first local electrical field $E_1$ is greater than the second local electrical field $E_2$.

In some embodiments, the second constricted passageway has a smaller cross-sectional area than the first constricted passageway.

In some embodiments, the second constricted passageway has a shorter length than the first constricted passageway.

In some embodiments, the first electrode is fabricated on a first end of the first constricted passageway, wherein the first end of the first constricted passageway is in the first reservoir.

In some embodiments, the first continuous microchannel has a saw-tooth-shaped cross-section.

In some embodiments, the first continuous microchannel has cross-section shape that establishes a first local dielectrophoresis (DEP) gradient, $(d\nabla|E|^2/dx_1)_{local}$ at the first constricted passageway and a different second local dielectrophoresis (DEP) gradient, $(d\nabla|E|^2/dx_2)_{local}$ at the second constricted passageway, wherein $x_1$ is a length parameter of the first constricted passageway, $x_2$ is a length parameter of the second constricted passageway.

In some embodiments, the first continuous microchannel has cross-section shape that establishes a first local dielectrophoresis (DEP) gradient, $(d\nabla|E|^2/dx_1)_{local}$ at the first constricted passageway and a different second local dielectrophoresis (DEP) gradient, $(d\nabla|E|^2/dx_2)_{local}$ at the second constricted passageway and a global DEP gradient $$\left(\frac{d\nabla|E|^2}{dx}\right)_{global} = \frac{\left(\frac{d\nabla|E|^2}{dx_2}\right)_{local} - \left(\frac{d\nabla|E|^2}{dx_1}\right)_{local}}{\Delta x},$$

wherein $x_1$ is a length parameter of the first constricted passageway, $x_2$ is a length parameter of the second constricted passageway, and $\Delta x$ is a parameter of distance between the first constricted passageway and the second constricted passageway.

In some embodiments, the first continuous microchannel has cross-section shape that establishes a first local electrical field $E_1$ in the first constricted passageway, a second local electrical field $E_2$ in the second constricted passageway, and wherein a magnitude of the first local electrical field $E_1$ is greater than the second local electrical field $E_2$, a first local dielectrophoresis (DEP) gradient, $(d\nabla|E|^2/dx_1)_{local}$ at the first constricted passageway, and a different second local dielectrophoresis (DEP) gradient, $(d\nabla|E|^2/dx_2)_{local}$ at the second constricted passageway, and a global DEP gradient $$\left(\frac{d\nabla|E|^2}{dx}\right)_{global} = \frac{\left(\frac{d\nabla|E|^2}{dx_2}\right)_{local} - \left(\frac{d\nabla|E|^2}{dx_1}\right)_{local}}{\Delta x},$$

wherein $x_1$ is a length parameter of the first constricted passageway, $x_2$ is a length parameter of the second constricted passageway, and $\Delta x$ is a parameter of distance between the first constricted passageway and the second constricted passageway.

In some embodiments, the first continuous microchannel has cross-section shape that establishes a first ratio of electric field E to local dielectrophoresis (DEP) gradient, $(d\nabla|E|^2/dx_1)_{local}$ at the first constricted passageway that is different than a second ratio of electric field E to local dielectrophoresis (DEP) gradient, $(d\nabla|E|^2/dx_2)_{local}$ at the second constricted passageway.

In some embodiments, the first continuous microchannel includes a plurality of constricted passageways formed in parallel between each successive pair of reservoirs of the plurality of reservoirs in order to increase the amount of the species collected and concentrated in each one of the plurality of reservoirs, including a third constricted passageway that is in parallel to the first constricted passageway between the first reservoir and the second reservoir, and a fourth constricted passageway that is in parallel to the second constricted passageway between the second reservoir and the third reservoir.

In some embodiments, the first continuous microchannel includes a plurality of constricted passageways formed in parallel between each successive pair of reservoirs of the plurality of reservoirs in order to increase the amount of the species collected and concentrated in each one of the plurality of reservoirs, including a third constricted passageway that is in parallel to the first constricted passageway between the first reservoir and the second reservoir, and a fourth constricted passageway that is in parallel to the second constricted passageway between the second reservoir and the third reservoir.

Some embodiments of the apparatus further include one or more additional electrodes operatively coupled to the first microchannel along the length of the first microchannel between the first electrode and the second electrode.

Some embodiments of the apparatus further include a pump connected to apply a pressure difference between the first reservoir and a last reservoir of the first microchannel in order to urge a flow of material through the first microchannel.

In some embodiments, the apparatus is configured to establish different dielectrophoretic gradients at each of the plurality of constricted passageways along the first microchannel.

In some embodiments, the apparatus includes a plurality of microchannels, each substantially the same as the first microchannel, fabricated in a single substrate.

In some embodiments, the present invention provides a method of separating particles. This method includes providing a substrate having a first continuous microchannel that is patterned with a plurality of sequential, constrictive insulating features to form a plurality of reservoirs including a first, second and third reservoir, and a plurality of constricted passageways including a first constricted passageway that connects the first reservoir to the second reservoir and a second constricted passageway that connects the second reservoir to the third reservoir, wherein the microchannel has walls that are electrically insulative; and applying a first local electrical field $E_1$ in the first constricted passageway and a second local electrical field $E_2$ in the second constricted passageway, and wherein a magnitude of the first local electrical field $E_1$ is greater than the second local electrical field $E_2$.

In some embodiments of the method, the second constricted passageway has a smaller cross-sectional area than the first constricted passageway.

In some embodiments of the method, the second constricted passageway has a shorter length than the first constricted passageway.

In some embodiments of the method, the second constricted passageway has different geometrical shape than the first constricted passageway.

In some embodiments of the method, the first electrode is on a first end of the first constricted passageway, wherein the first end of the first constricted passageway is in the first reservoir. In some such embodiments, the first constricted passage is a capillary tube having the first electrode formed on an end of the capillary tube.

In some embodiments of the method, the first continuous microchannel has a saw-tooth-shaped cross-section.

Some embodiments of the method further include establishing a first local dielectrophoresis (DEP) gradient, $(d\nabla |E|^2/dx_1)_{local}$ at the first constricted passageway and a different second local dielectrophoresis (DEP) gradient, $(d\nabla |E|^2/dx_2)_{local}$ at the second constricted passageway, wherein $x_1$ is a length parameter of the first constricted passageway, $x_2$ is a length parameter of the second constricted passageway.

Some embodiments of the method further include establishing a first local dielectrophoresis (DEP) gradient, $(d\nabla |E|^2/dx_1)_{local}$ at the first constricted passageway and a different second local dielectrophoresis (DEP) gradient, $(d\nabla |E|^2/dx_2)_{local}$ at the second constricted passageway and a global DEP gradient $$\left(\frac{d\nabla |E|^2}{dx}\right)_{global} = \frac{\left(\frac{d\nabla |E|^2}{dx_2}\right)_{local} - \left(\frac{d\nabla |E|^2}{dx_1}\right)_{local}}{\Delta x},$$

wherein $x_1$ is a length parameter of the first constricted passageway, $x_2$ is a length parameter of the second constricted passageway, and $\Delta x$ is a parameter of distance between the first constricted passageway and the second constricted passageway.

Some embodiments of the method further include establishing a first local electrical field $E_1$ in the first constricted passageway, a second local electrical field $E_2$ in the second constricted passageway, and wherein a magnitude of the first local electrical field $E_1$ is greater than the second local electrical field $E_2$, a first local dielectrophoresis (DEP) gradient, $(d\nabla |E|^2/dx_1)_{local}$ at the first constricted passageway, and a different second local dielectrophoresis (DEP) gradient, $(d\nabla |E|^2/dx_2)_{local}$ at the second constricted passageway, and a global DEP gradient $$\left(\frac{d\nabla |E|^2}{dx}\right)_{global} = \frac{\left(\frac{d\nabla |E|^2}{dx_2}\right)_{local} - \left(\frac{d\nabla |E|^2}{dx_1}\right)_{local}}{\Delta x},$$

wherein $x_1$ is a length parameter of the first constricted passageway, $x_2$ is a length parameter of the second constricted passageway, and $\Delta x$ is a parameter of distance between the first constricted passageway and the second constricted passageway.

In some embodiments of the method, the first continuous microchannel has cross-section shape that establishes a first ratio of electric field E to local dielectrophoresis (DEP) gradient, $(d\nabla |E|^2/dx_1)_{local}$ at the first constricted passageway that is different than a second ratio of electric field E to local dielectrophoresis (DEP) gradient, $(d\nabla |E|^2/dx_2)_{local}$ at the second constricted passageway.

In some embodiments, the present invention provides includes a punctuated microgradient device fabricated according to one or more processes or sub-processes of the methods set forth herein.

In some embodiments, the present invention provides a computer-implemented method that includes calculating in a computer a shape for a first microchannel having a plurality of sequential, constrictive insulating features to form a plurality of reservoirs including a first, second and third reservoir, and a plurality of constricted passageways including a first constricted passageway that connects the first reservoir to the second reservoir and a second constricted passageway that connects the second reservoir to the third reservoir, such that the first microchannel has cross-section shape that establishes a first local electrical field $E_1$ in the first constricted passageway and a second local electrical field $E_2$ in the second constricted passageway, wherein a magnitude of the first local electrical field $E_1$ is greater than the second local electrical field $E_2$; storing in the computer a representation of the calculated first microchannel shape; and photolithographically forming a first microchannel in a substrate using the stored representation of the calculated first microchannel shape in order to fabricate a punctuated microgradient device, wherein the first microchannel is formed with a first electrode and a second electrode both operatively coupled to the first microchannel and configured to establish an electric field E within the microchannel. Some embodiments of the present invention include a punctuated microgradient device fabricated according to this method.

In some embodiments, the present invention provides a computer-implemented method that includes calculating in a computer a shape for a first microchannel having a plurality of sequential, constrictive insulating features to form a plurality of reservoirs including a first, second and third reservoir, and a plurality of constricted passageways including a first constricted passageway that connects the first reservoir to the second reservoir and a second constricted passageway that connects the second reservoir to the third reservoir, such that the first microchannel has cross-section shape that establishes a first local electrical field $E_1$ in the first constricted passageway and a second local electrical field $E_2$ in the second constricted passageway, and a first dielectrophoresis (DEP) parameter, $\nabla |E_1|^2$ at the first constricted passageway and a different second dielectrophoresis (DEP) parameter, $\nabla |E_2|^2$ at the second constricted passageway, wherein a magnitude of the first local electrical field $E_1$ is greater than the second local electrical field $E_2$; storing in the computer a representation of the calculated first microchannel shape; and photolithographically forming a first microchannel in a substrate using the stored representation of the calculated first microchannel shape in order to fabricate a punctuated microgradient device, wherein the first microchannel is formed with a first electrode and a second electrode both operatively coupled to the first microchannel and configured to establish an electric field E within the microchannel. Some embodiments of the present invention include a punctuated microgradient device fabricated according to this method.

In some embodiments, the present invention provides a non-transitory computer-readable medium having instructions stored thereon for causing a suitably programmed computer to perform a computer-implemented method that includes calculating in a computer a shape for a first microchannel having a plurality of sequential, constrictive insulating features to form a plurality of reservoirs including a first, second and third reservoir, and a plurality of constricted passageways including a first constricted passageway that connects the first reservoir to the second reservoir and a second constricted passageway that connects the second reservoir to the third reservoir, such that the first microchannel has cross-section shape that establishes a first local electrical field $E_1$ in the first constricted passageway and a second local electrical field $E_2$ in the second constricted passageway, wherein a magnitude of the first local electrical field $E_1$ is greater than the second local electrical field $E_2$; and storing in the computer a representation of the calculated first microchannel shape. Some embodiments further include the computer and its storage, which is configured to read the instructions from the non-transitory computer-readable.

In some embodiments, the present invention provides a non-transitory computer-readable medium having instructions stored thereon for causing a suitably programmed computer to perform a computer-implemented method that includes calculating in a computer a shape for a first microchannel having a plurality of sequential, constrictive insulating features to form a plurality of reservoirs including a first, second and third reservoir, and a plurality of constricted passageways including a first constricted passageway that connects the first reservoir to the second reservoir and a second constricted passageway that connects the second reservoir to the third reservoir, such that the first microchannel has cross-section shape that establishes a first local electrical field $E_1$ in the first constricted passageway and a second local electrical field $E_2$ in the second constricted passageway, and a first dielectrophoresis (DEP) parameter, $\nabla|E_1|^2$ at the first constricted passageway and a different second dielectrophoresis (DEP) parameter, $\nabla|E_2|^2$ at the second constricted passageway, wherein a magnitude of the first local electrical field $E_1$ is greater than the second local electrical field $E_2$; and storing in the computer a representation of the calculated first microchannel shape.

As set forth in the above description and the attached figures, the present invention provides devices and methods to separate and concentrate target species at a microliter scale and using only picograms of target material. In some embodiments, a punctuated continuous microchannel is provided, the microchannel having a plurality of sequential, constrictive insulating features to form a plurality of reservoirs including a first, second and third reservoir, and a plurality of constricted passageways including a first constricted passageway that connects the first reservoir to the second reservoir and a second constricted passageway that connects the second reservoir to the third reservoir. A voltage is applied to the microchannel to create different electrical fields and/or different dielectrophoresis (DEP) gradients at each of the plurality of constricted passageways in order to separate species that have differing ratios of electrokinetic mobility to dielectrophoretic mobility.

EXAMPLE 3

Differentiation of *Escherichia coli* Serotypes Using DC Gradient Insulator Dielectrophoresis Bacteria play a significant role in both human health and disease. An estimated 9.4 million cases of foodborne illness occur in the United States each year. As a result, rapid identification and characterization of microorganisms remains an important research objective. Despite limitations, selective culturing retains a central role amongst a cadre of identification strategies. For the past decade, separations-based approaches to rapid bacterial identification have been under investigation. Gradient insulator dielectrophoresis (g-iDEP) promises benefits in the form of rapid and specific separation of very similar bacteria, including serotypes of a single species. Furthermore, this approach allows simultaneous concentration of analyte, facilitating detection and downstream analysis. Differentiation of three serotypes or strains of *Escherichia coli* bacteria is demonstrated within a single g-iDEP microchannel, based on their characteristic electrokinetic properties. Whole cells were captured and concentrated using a range of applied potentials, which generated average electric fields between 160 and 470 V/cm. Bacteria remained viable after exposure to these fields, as determined by cellular motility. These results indicate the potential g-iDEP holds in terms of both separatory power and the possibility for diagnostic applications.

Introduction

It is believed that over $10^{30}$ bacteria live on planet Earth and their biomass may exceed that of all other organisms combined. [1] The average human intestine is home to about $10^{14}$ bacteria—a microbiome composed of 500-1000 individual species. [2] Bacteria in the environment, of course, represent an even more complex array of species and niches. Typically these organisms are commensal or mutualistic, conferring some benefit to each other or their host. Some species, however, are pathogenic. Most strains of *Escherichia coli*, for instance, are innocuous to humans. However as recent headlines note, some can cause intoxication and infection where resulting syndromes may lead to death.

Relatively little is known about the immense diversity of species comprising the gut flora that crowds the human intestine. Many species remain unknown since most identification strategies require culturing—the growth of particular species in artificial environment—and many species will not accommodate this strategy. False negatives have been documented to reach at least seventy percent when conventional microbiological culture is used alone. [3-5]

In practical settings, bacteria are identified by molecular—and microbiologists, who use an ensemble of tests to accomplish this task. Species and strains are identified and grouped by phenotypic characteristics such as appearance and immunologic reactivity, and genotypic characteristics. Specific examples of tests used for classification include differential staining, selective culturing, serological typing, nucleotide sequence recognition, and flow cytometry. [6] Many of these methods require preparation and growth of cultures, which significantly extends the time required for analysis. Culturing also reduces the possibility of determining the abundance or population diversity of microbes in the original sample. While nucleic acid amplification methods minimize or eliminate the need for culturing, DNA isolation and purification can be laborious. Emerging commercial approaches involving rapid PCR may reduce the time and preparation required for such tests, but involve bench-top instruments, only detect previously identified targets for which sequences are established, and typically only screen for panels of very common pathogens. As such, these approaches do not lend themselves to the development of rapid and broad field-based analysis. [7]

A separations-based strategy for isolating and concentrating intact microorganisms could offer significant benefits over traditional approaches. Rapid identification and quantitation could provide revolutionary benefits in scientific, clinical, and environmental applications. A number of scientists, for over fifty years, have recognized that different cells have unique electrical properties and furthermore that those properties can be detected and used to initiate separations between different types of cells. Early work focused on sensing unique resistive and dielectric properties via impedance spectroscopy. These works often investigated the electric properties of single species by applying an alternating potential across the cells and recording current with respect to frequency. [8-10] Others attempted to bifurcate samples into two analyte populations (e.g. leukemic cells and erythrocytes). [11-14] This research defined many unique and quantifiable differences between bacteria and many other types of cells.

A number of researchers have pursued capillary electrophoresis (CE) of microorganisms. [15] However, designing such a separation scheme faces many hurdles. As targets for analytical separations, bacteria and other microbes are both attractive and uniquely challenging. After several years developing novel approaches to CE of bacteria, Armstrong et al. identified a few of the chief difficulties involved with bacterial CE separations. These include long separation times, poor specificity, sensitivity of the analyte to the surrounding analytical environment, requirements for sample purity, and microbe aggregation. [16] CE separations of bacteria have yielded interesting results, but are typically plagued by band broadening. This decreases selectivity and separation efficiency. Armstrong et al. introduced the use of poly(ethylene oxide) (PEO) as a dynamic additive in bacterial separations. This dramatically increased apparent separation efficiency, however, peak purity was not assessed and the narrow peaks were determined to result from microbial aggregation.

Innovations using mass spectrometry (MS) provide an interesting alternative route to microbe identification. MS is typically used to identify small and large molecules. Identification of cells involves breaking them into ionized molecular fragments and measuring mass/charge ratio of the products. Cells can be identified by the characteristic fingerprint they produce in such analyses. Mass-spectrometry faces many challenges, however, including the need for sample purity, broad chemical differences in cell species, and variations between stages of cell development.

Recent electrokinetic (EK) approaches to the manipulation and analysis of microbes and other cells have demonstrated the potential for significant improvements over traditional methods. Dielectrophoresis (DEP) offers tantalizing benefits in the form of extremely rapid and specific separations that can occur while simultaneously concentrating the analyte. Dielectrophoretic force results from the interaction between permanent or field-induced dipoles and a spatially inhomogeneous electric field. DEP acts upon analyte in concert with other field-induced forces such as electrophoresis (EP) and electroosmotic flow (EOF). Together, these three forces provide multiple force vectors with which to query a variety of analyte properties, including but not limited to particle size, structure, surface charge, charge heterogeneity, polarizability, and permittivity differences between the cells and the buffer. These traits can vary widely between cells and microbes that otherwise appear and behave similarly. As one example, DEP has been used to differentiate erythrocytes based on antigen expression. [17]

Early implementations of DEP used patterned electrodes to generate AC field gradients. Separations were based on the characteristic crossover frequency, where net dielectrophoretic force switches from positive (up-gradient) to negative (down-gradient). Later work used electrically insulating structures to impinge upon field lines and induce a local gradient. Beginning in 2002, this work was rapidly expanded. [18,19] The use of insulator-based dielectrophoresis (iDEP) ameliorated many of the problems associated with traditional DEP experiments, which included electrolysis within separation zones, joule heating, cellular damage, and complex fabrication procedures. DC iDEP also enabled the simultaneous use of field-driven flow through separation zones.

The work presented here utilizes an approach to iDEP first introduced in 2007, in which insulating sawtooth features along the sides of a microchannel create electric field inhomogeneities. [20] Progressive changes in the tooth geometry create distinct zones of increasing local field gradient along the length of the channel. This progression of local maxima yields a secondary macro-gradient globally across the device. Analyte is driven through the channel by a combination of EP and EOF. Particles traveling down the channel encounter zones of increasing DEP force as they approach each set of opposing teeth. When DEP force is sufficient to counter the combination of EP and EOF, particles are trapped and prevented from further translation down the channel. This causes particles to stop at discrete and unique points along the channel, based on their individualized electrokinetic properties.

Using this approach, our group is refining the separation of bacterial species and strains based on their physical and electrical properties. The work presented here is unique for three reasons. First, it uses a linear separation mode combining electrophoresis, electroosmotic flow, and dielectrophoresis, where a distinctive balance point can be found for an analyte based on the ratio of its electrokinetic mobility (the sum of electrophoretic and electroosmotic mobilities) and dielectrophoretic mobility. Second, it is an extremely high-resolution separation scheme, better than many traditional electrophoretic and dielectrophoretic strategies. Third, we demonstrate that individual strains of *E. coli* can be differentiated. This suggests an opportunity to begin to identify bacteria by their electric properties. Specifically, this work indicates that three serotypes of *E. coli* can be differentiated within an appropriately designed g-iDEP microchannel, including differentiation of pathogenic from non-pathogenic types.

Materials and Methods

Microdevice Fabrication

The geometry of the sawtooth channel has been described previously. In brief, it consists of adjoined triangular units aligned along each side of a channel (FIGS. 1A-1C). Successive narrowed segments are formed where the tips of each set of opposing triangles draw together. These narrowed regions are considered gates for this discussion. The equilateral, triangular units increase in size along the length of the channel, causing the apices of opposing triangles or teeth to gradually converge towards the channel centerline. For this particular case, the channel length, width, and depth were 4.1 cm, 1000 μm, and 14±1 μm (average between templates), respectively. The initial gate height was 945 μm and the final one 27 μm.

The microfluidic devices used in these experiments were fabricated using soft lithography. [21,22] The sawtooth channels were patterned on 4-inch Si wafers using AZ P4620 positive photoresist (AZ Electronic Materials, Branchburg, N.J.) and contrast enhancement material CEM388SS (Shin-Etsu MicroSi, Inc., Phoenix, Ariz.). The photoresist was exposed with a high-fidelity chrome photomask, and then developed. PDMS (Sylgard 184, Dow/Corning, Midland, Mich.) was poured over the resulting templates and allowed to cure at 70C for one hour. PDMS casts were then peeled from the template wafers, trimmed to size, and punched with 2-mm diameter holes for access to the round, terminal reservoirs at each end of the channel.

Finalized devices were constructed from polydimethylsiloxane (PDMS) casts bonded to a glass coverplate. This approach yielded microfluidic channels with three walls of PDMS and one of glass. The two materials were treated with oxygen plasma in a Tegal asher (PlasmaLine 411, Tegal Corporation, Petaluma, Calif.) and then allowed to seal upon contact.

Cell Culture and Labeling

Three strains of *Escherichia coli* were obtained including serotypes O157:H7, strain 465-97; O55-H7; and a quality control strain O6:K1:H1, equivalent to ATCC 25922. Each strain represents a different serogroup, and will be referred to by serotype only.

*E. coli* seed stock was stored on biobeads in Brucella Broth with 10% glycerol at −80° C. Ten-mL aliquots of sterile lysogeny broth (LB) (Sigma-Aldrich Co., St. Louis, Mo.) were placed in culture tubes. Each tube was inoculated with one of the strains then incubated overnight at 37° C. This allowed each culture to reach late log phase, with a cell concentration of approximately 109 cells/mL. Following incubation, 500-µL aliquots of each cell culture were centrifuged at 4000 g for 3 minutes. The supernatant was discarded and the cell pellet resuspended by adding 1 mL 2 mM phosphate buffer at a pH of 7.4 and mixing with a vortexer for 10-15 seconds. This process was repeated two more times in order to wash the cells and remove the LB broth.

Cells were labeled using Vybrant DiO fluorescent dye (Invitrogen). [23-25] Excitation and emission wavelengths for this dye are 484 and 501 nm, respectively. A 5-µL aliquot of dye was added to each 1-mL suspension of washed cells. These were incubated in a 37° C. water bath for approximately 20 minutes. The samples were then washed three times in order to eliminate free dye. This was accomplished by centrifuging and resuspending the cells in phosphate buffer as described above, with the exception that the final buffer solution contained 4 mg/mL bovine serum albumin (BSA). Throughout the labeling process, exposure to ambient light was minimized in order to prevent photobleaching. Examination of the dispersed, suspended cells using a microscope revealed that they were individual, intact cells, with minimal aggregation.

Experimental

The microdevice was placed on the stage of an Olympus IX70 inverted microscope with a ×4 or ×10 objective for observation and data collection. Samples were introduced into the microdevice by pipetting ~20 µL of cell suspension into the inlet reservoir. Hydrodynamic flow was balanced by pipetting a similar volume of buffer into the outlet reservoir. Particle motion within the channel was observed in order to monitor and ensure stasis of flow. A mercury short arc lamp (H30 102 w/2, OSRAM) was used for illumination. An Olympus DAPI, FITC, Texas Red triple band-pass cube (Olympus, Center Valley, Pa.) was used for fluorescence microscopy. Both still images and video were collected with a monochrome QICAM cooled CCD camera (QImaging, Inc., Surrey, BC) and Streampix V image capture software (Norpix, Inc., Montreal, QC).

Platinum electrodes with a diameter of 0.404 mm (Alfa Aesar, Ward Hill, Mass.) were inserted through the PDMS access ports into the terminal reservoirs. They were then connected to a HVS448 3000D high voltage sequencer (Labsmith, Inc., Livermore, Calif.).

Bacteria were captured in both deionized $H_2O$ (DI-$H_2O$) and 2 mM phosphate buffer at a pH of 7.4. The conductivities of these solutions were 55.3 and 343 µS/cm, respectively. DI-$H_2O$ and buffer solutions also contained BSA ranging in concentration from 0-8 mg/mL. The experiments described here contained BSA at 4 mg/mL. DC potentials applied across the device ranged from 0-3000 V in 100 V increments. These potentials correspond to average field strengths ($E_{app}$=V/4.1 cm) of 0-732 V/cm and increments of approximately 24 V/cm.

Particle image velocimetry (PIV) measurements were used to determine the EK velocity of the bacteria. Cell motion was observed within the straight portions of the microchannel proximal to each reservoir. Local electric field strength was determined using COMSOL Multiphysics modeling. These values were used along with velocity data to estimate EK mobilities.

Mathematical Modeling

Electric field characteristics in the microchannel were numerically modeled with COMSOL Multiphysics software (COMSOL, Inc., Burlington, Mass.). The model consisted of properly scaled 2D geometry of the main channel, excluding the device reservoirs. A 2D approximation greatly simplifies the calculations and was used since the electrical potential is presumed to vary minimally across the relatively small depth of the microchannel. The conductivity and relative permittivity of the medium were set to 1.2 S/m and 78, respectively.

Safety Considerations

Organisms used in this experiment were Biosafety Level I or II. All experiments were carried out in an approved BSL II laboratory within accordance with the current version of the CDC/NIH BMBL publication.

Results

Three strains of *E. coli*, expressing O157:H7, O55:H7, or O6:K1:H1 antigenic phenotypes, with each being a different serotype, were investigated within g-iDEP devices. Their behavior was examined primarily at the final three sets of gates within the microchannel, namely those with a gate pitch of 300 µm, 90 µm, or 27 µm. Gate pitch refers to the distance between the points of opposing teeth. The magnitude of the electric potential applied across the device was recorded in terms of ΔV divided by 4.1 cm, or the overall length of the channel ($E_{app}$). The value of $E_{app}$ was varied along with the duration of applied potential ($t_{app}$). The location of collection was noted in terms of gate pitch.

Electrokinetic and dielectrophoretic behaviors of the bacteria were broadly consistent with prior observations of other samples in g-iDEP devices. Upon application of potential, bulk motion of particles was initiated towards the outlet reservoir, which housed the cathode, consistent with expected EOF direction and charge state of bacteria. [26] No particle capture was observed in the wide-gated segments of the sawtooth channel (gate pitch>300 µm). Within these regions, all visible material traveled consistently towards the cathode in the outlet reservoir. Capture resulted in the formation of crescent-shaped bands of concentrated particles immediately upstream of a given gate. [27,22,28,20] Unique capture and concentration of all three *E. coli* serotypes was observed.

All three serotypes were captured at 27 µm gates, with statistically significant differences in Eapp required for capture of each. Only two serotypes were captured at 90 μm gates, and one serotype at 300 μm gates. The behavior of O6:K1:H1 and O55:H7 indicate that the difference in Eapp required for capture of different serotypes increases at larger gate pitches.

The amount of material captured at a particular gate was dependent upon the magnitude and duration of the applied electric field. Below a particular value of $E_{app}$ no capture occurred, even over extended periods of time. That threshold value is referred to as $E_{onset}$ and occurred after sufficient potential was applied across the device, causing particles to collect in characteristic zones near the entrance to a gate. Capture was monitored by local fluorescence intensity. Material continued to capture while potential was applied. Since collection varied with both $t_{app}$ and $E_{app}$, data was collected and compared at consistent time points following application of the electric field. By holding $t_{app}$ constant, the dependence of capture on $E_{app}$ could be investigated. Above $E_{onset}$, the rate of particle accumulation increased with $E_{app}$ (FIGS. 3A-3B). This was observed both via qualitative image analysis and fluorescence intensity measurements.

Integrated fluorescence intensity (FI) was measured within a small region of interest (ROI) at expected capture zones. Plots of these data corresponded with qualitative observations. Specifically, measured values of FI increased rapidly with $t_{app}$ above $E_{onset}$ (FIG. 4a). FI measurements were taken at $t_{app}$=5 s and plotted versus $E_{app}$, elucidating characteristic behaviors for each serotype at the various gate pitches. At values of $E_{app}$ greater than $E_{onset}$, FI continued to increase before eventually leveling off. This yielded plots with a roughly sigmoidal shape (FIG. 4b).

Repeated experiments demonstrated similar behavior. FIG. 5 shows the average integrated fluorescence intensity for data collected from five different devices with separate bacterial preparations of serotype O6:K1:H1. Error bars indicate the standard deviation of each set.

The inflection points of the sigmoidal curves shown in FIG. 4b were used as the serotype-specific $E_{onset}$ values for appreciable capture. These $E_{onset}$ values were plotted versus gate pitch for each serotype (FIG. 6). $E_{onset}$ values for O6:K1:H1 were 163±31, 259±52, and 427±53 V/cm for the 27-, 90-, and 300-μm gates, respectively. $E_{onset}$ values for O55:H7 were 290±16 and 470±8 V/cm at 27- and 90-μm gates. For O157:H7, $E_{onset}$ was 324±25 V/cm at 27-μm gates. The results indicate statistically significant differences in capture behavior for the three serotypes of E. coli bacteria.

Unstained samples of each E. coli serotype were also used on microdevices and observed using a combination of brightfield and darkfield microscopy. Capture data from these runs agreed identically with that obtained using fluorescently-labeled samples, suggesting that the electrokinetic effects of the membrane-intercalating dye were negligible within the framework of this application.

Discussion

In order to understand behavior of these species in a g-iDEP microchannel, it's instructive to briefly consider their physicochemical characteristics. The cell surface of gram-negative bacteria such as E. coli typically consists of various phospholipids, membrane proteins, and a lipopolysaccharide (LPS) coat. [29] The lipopolysaccharide layer on the outer leaflet of the E. coli membrane (associated with the O antigen) is expected to contribute significantly to negative surface charge, due to the presence of both carboxylic acid and phosphate moieties. [30] Large-scale surface features such as flagella and fimbriae also affect the cell's surface properties. [31] Various strains of E. coli differ in their biochemical and physical phenotypes. Distinctions between strains can manifest in terms of protein expression, glycosylation, LPS structure, as well as differences in their flagella, fimbriae, and internal structures. [32] Considered together, these phenotypic differences can impact the charge and polarizability of E. coli cells, and thus contribute to different electrophoretic and dielectrophoretic mobilities.

Utilizing g-iDEP methodology presents unique opportunities to exploit these differences to generate separations. Although the complexity of biological objects like bacterial cells creates unique challenges, it also furnishes a rich set of vectors for separatory differentiation. Demonstrations of bioparticle capture using this approach have shown rapid, specific capture from heterogeneous samples For the purposes of this discussion, EK motion refers to the transport of particles induced by the application of an external electric field. In these experiments EK transport included the effects of EP and EOF, which are both directly proportional to electric field strength. In the case of small particles, EP force is proportional to net surface charge as well as field strength. At or below neutral pH, E. coli bacteria possess a negative surface charge. As such, EP force will be directed toward positive electric potential. Above a pH of ~4, glass and oxidized PDMS surfaces carry a negative surface charge. This produces EOF in the opposite direction, or towards negative electric potential. In these experiments pH was maintained at 7.4. As a result, the observed motion of all bacteria towards the negative electrode indicated that under these conditions the electroosmotic mobility (μEO) exceeded their electrophoretic mobility (μEP) of the bacteria. Although dominant μEO) determined the direction of transport, differences in μEP between analytes still contribute significantly to net electrokinetic mobility (μEK) and the resulting translational velocity of particles.

Electrophoretic mobilities for various serotypes of E. coli, including O157:H7, have been reported in the range of $-0.2 \times 10^{-4}$ to $-1.4 \times 10^{-4}$ cm2Ns at or near neutral pH.[33] However, these values vary with buffer pH and ionic strength. Within the g-iDEP microchannel, μEP was not measured directly. Instead, an effective estimated μEK was determined via particle tracking. Positive values support that EOF exceeded EP force. Values of μEK determined for E. coli in the g-iDEP microchannel ranged from $1.2 \times 10^{-4}$ to $2.5 \times 10^{-4}$ cm$^2$/Vs.

Theoretical descriptions of dielectrophoretic behaviors of cells utilize multishell models to approximate cell structure and heterogeneity.[34] In these models, cells are treated as bodies consisting of onion-like layers with varying electrical properties. E. coli can be approximated as a prolate ellipsoid, with two finite-thickness shells encapsulating the cytoplasm. The outer and inner shells represent the LPS layer and cell membrane, respectively. The cytoplasm and each shell are attributed unique values for permittivity and conductivity. These models indicate that at low frequencies, including DC fields, the conductivity of the LPS layer ($\sigma_{wall}$) and cell membrane ($\sigma_{mem}$) factor significantly into the dielectric properties of the cell. [35] The dielectric properties of bacteria have yet to be precisely characterized. No alternative or independent quantitative information exists for both size and dielectric differences between strains of E. coli. Work performed by Castellarnau et al. using AC DEP focused on crossover frequencies of isogenic mutants of one strain of E. coli and further utilized a multishell model to estimate conductivities of cell cytoplasm, membrane, and wall. The geometric parameters used for these calculations involved an ellipsoid with axes a=3/2 and b=a/2, cell membrane thickness of 8 nm, and cell wall thickness of 50 nm. Using this approach, respective values for $\sigma_{wall}$ and $\sigma_{mem}$ were estimated to be 58×10$^{-3}$ S/m and 259×10$^{-6}$ S/m for *E. coli* strain 5K. These conductivities are expected to vary significantly between strains of bacteria, based on their chemical makeup and protein expression profiles. Castellarnau et al. found that these values may vary by up to 70 percent for isogenic mutants of a single strain. Their experiments demonstrated that isogenic mutants of *E. coli*, differing at one allele, express sufficiently divergent phenotypes for different dielectrophoretic behavior.

Discussions of bacterial dielectric properties typically stop short of assigning or estimating specific values for $\mu_{DEP}$. An experimental value of $\mu_{DEP}$ can be deduced from g-iDEP data by observing that the electrokinetic ($F_{EK}$) and dielectrophoretic forces ($F_{DEP}$) balance at the noted gate for the appropriate $E_{onset}$. This estimation was only calculated for the serovar that was captured at all three gates, O6:K1:H1, and resulting a value of $-1.4\pm0.9\times10^{-17}$ m$^4$/V$^2$s—a reasonable value compared to other particles measured in insulator dielectrophoretic systems (polystyrene, 1 micron, $-2\times10^{-16}$ m4/V$^2$s). [36] This mobility can be used along with the local electric field strength to estimate the magnitude of the focusing forces exerted upon a single captured bacterium. For $E_{onset}$ at a 27 μm gate COMSOL Multiphysics modeling indicated centerline values of $\nabla|E|^2$ were approximately $1.0\times10^{15}$ V$^2$/m$^3$. For this calculation, an *E. coli* cell was treated as a prolate ellipsoid with major axis a=2 μm and minor axis b=0.5 μm. Using these assumptions and calculated values, the force is approximately 0.2 nN ($F_{EK}\leq-F_{DEP}=2\times10^{-10}$ N).

The general features of the observed capture of *E. coli* in a sawtooth g-iDEP device are consistent with previous results obtained using cells and other bioparticles. The characteristic behaviors have been described in detail elsewhere. [27] Briefly, the insulating PDMS constrictions yield intense electric field gradients. As particles approach a gate, they experience increasing dielectrophoretic force, which approaches a local maximum value. Negative DEP force is directed away from these regions, thus maximally opposing net EK force just before a particle passes the center of a gate. The magnitude of local electric field strength is proportional to $E_{app}$ and inversely proportional to cross-sectional area. Thus local magnitudes of $\nabla|E|^2$ and resulting DEP force are a function of both $E_{app}$ and gate pitch. Trapping occurs when DEP force exerted on a particle exceeds net EK force.

The dependence of capture on $E_{app}$ and gate pitch was observed for all three serotypes (FIG. 6). A difference in $E_{app}$ required for capture at a given gate between any two particle types indicates that they possess either differing $\mu_{EK}$, $\mu_{DEP}$, or both. A sufficient difference in these factors indicates that two particles could be differentiated.

When $E_{app}$ was less than 100 V/cm, dielectrophoretic force was insufficient for capture of any cells. Capture at field strengths less than this value would require either a smaller gate pitch or a reduction in EK velocity. The latter could potentially be achieved by a reduction in EOF. Values of $E_{app}$ above approximately 730 V/cm were unattainable due to equipment constraints. This represents the maximum potential of 3000 V that could be applied to the channel using the existing power supply. Application of higher potentials is also impractical due to excessive joule heating, which causes bubble formation within the channel, particularly where a large potential drop occurs across narrow gates.

Variables that could not precisely controlled or quantitated, such as bacterial cell count, staining efficiency, pressure-driven and electroosmotic flow control, slightly varying properties for the individual cells, and photobleaching effects all contribute to the overall variance.

All samples were inspected at relatively high magnification before and after collection to observe the typical swimming and tumbling behaviors characteristic of the serotype. In all cases investigated, similar behaviors were observed for both conditions, suggesting that the high electric field and possible Joule heating did not negatively impact the bacteria in a significant manner. This is attributed to the relatively weak external field strength compared to local zeta potential/lipid bilayer field strength, which are typically several orders of magnitude higher than those estimated to be present within these devices.

These results show that O157:H7, O55:H7, and O6:K1:H1 serotypes of *E. coli* can be differentiated using g-iDEP operated with DC fields. In different pathogenic and non-pathogenic *E. coli* serotypes, small differences in cell structure, membrane, and wall composition are shown to be sufficient for differentiating populations. Current literature sources offer scant quantitative data regarding physical and electrical differences between strains of *E. coli*. Strain-to-strain variations in mean size or geometry are unknown. If such variation existed, however, it could be expected to contribute significantly to differences in both electrophoretic and dielectrophoretic force. Strain-specific differences in the biochemical makeup of the cell membrane and wall are likely to affect bacterial surface charge and conductivity. These parameters will in turn yield characteristic differences in electrophoretic and dielectrophoretic force.

Although it has not been demonstrated here, it is plausible that simultaneous separation and capture of all three serotypes within a single channel is achievable. This supports the idea that this approach can be adapted for future separation and identification of similar bacteria in microfluidic devices. However, this would require restructuring the progression of gate pitch along the channel. Future efforts will evaluate the implementation and efficiency of such separations. Specifically, advancements in channel geometry and surface treatments, along with the possible use DC-offset AC fields promise to extend the abilities and applicability of this approach.

While the work presented here must adapt to the semantics of existing microbiological methods, the mechanism of identification and differentiation pursued here differs. Large-scale, phenotypic differences arise from molecular origins, which are concomitantly associated with identifiable and characteristic variation of cellular electric properties. With sufficient separatory resolution, gradient insulator-based dielectrophoresis (g-iDEP) will enable separation of many if not all of the categories currently used by microbiologists.

CONCLUSION

Using a g-iDEP strategy implemented with a pattern of sawtooth insulators has demonstrated differentiation of three serotypes of *E. coli* bacteria. While previous work has shown differentiation of bacteria based on species or live/dead state, this is the first demonstration of serotype differentiation using DC fields or insulator-based dielectrophoresis. Capture behavior was consistent with electric field modeling and overlapped with capture zones predicted from negative DEP forces. The results presented here indicate that all three serotypes could be discretely captured within a single separatory channel. Further modeling and design will facilitate optimization of g-iDEP channel geometry for the separation and capture of similar bioanalytes from complex mixtures. Such improvements will aid the development of new bioanalytical tools that enable the identification of microbes through precise and rapid separations.

List of Abbreviations for Example 3: DC, direct current; EP, electrophoresis; EOF, electroosmotic flow; DEP, dielectrophoresis; iDEP, insulator dielectrophoresis; g-iDEP, gradient-insulator-based dielectrophoresis

REFERENCES FOR EXAMPLE 3

1. Whitman WB, Coleman DC, Wiebe WJ (1998) Prokaryotes: The unseen majority. Proc Natl Acad Sci USA 95 (12):6578-6583. doi:10.1073/pnas.95.12.6578
2. Hooper LV, Gordon JI (2001) Commensal host-bacterial relationships in the gut. Science 292 (5519):1115-1118. doi:10.1126/science.1058709
3. Agata EMCD, Gautam S, Green WK, Tang Y-W (2002) High Rate of False-Negative Results of the Rectal Swab Culture Method in Detection of Gastrointestinal Colonization with Vancomycin-Resistant Enterococci. Clinical Infectious Diseases 34 (2):167-172. doi:10.1086/338234
4. Benjamin RJ, Wagner SJ (2007) The residual risk of sepsis: modeling the effect of concentration on bacterial detection in two-bottle culture systems and an estimation of false-negative culture rates. Transfusion 47 (8):1381-1389. doi:10.1111/j.1537-2995.2007.01326.x
5. Scallan EG, P.M.; Angulo, F.J.; Tauxe, R.V.; Hoekstra, R.M. (2011) Foodborne Illness Acquired in the United States—Unspecified Agents. Emerging Infectious Diseases 17 (1):16-22
6. Black JG (1996) Microbiology: principles and applications. Prentice Hall,
7. Tenover FC (2010) Potential impact of rapid diagnostic tests on improving antimicrobial use. In: Bush K (ed) Antimicrobial Therapeutics Reviews, vol 1213. Annals of the New York Academy of Sciences. pp 70-80. doi:10.1111/j.1749-6632.2010.05827.x
8. Suehiro J, Noutomi D, Shutou M, Hara M (2003) Selective detection of specific bacteria using dielectrophoretic impedance measurement method combined with an antigen-antibody reaction. Journal of Electrostatics 58 (3-4):229-246. doi:10.1016/s0304-3886(03)00062-7
9. Gascoyne PRC, Noshari J, Becker FF, Pethig R (1994) Use of Dielectrophoretic Collection Spectra for Characterizing Differences Between Normal and Cancerous Cells. IEEE Transactions on Industry Applications 30 (4):829-834. doi:10.1109/28.297896
10. Huang Y, Wang XB, Becker FF, Gascoyne PRC (1996) Membrane changes associated with the temperature-sensitive P85(gag-mos)-dependent transformation of rat kidney cells as determined by dielectrophoresis and electrorotation. Biochimica et Biophysica Acta-Biomembranes 1282 (1):76-84
11. Becker FF, Wang XB, Huang Y, Pethig R, Vykoukal J, Gascoyne PRC (1994) THE REMOVAL OF HUMAN LEUKEMIA-CELLS FROM BLOOD USING INTERDIGITATED MICROELECTRODES. Journal of Physics D-Applied Physics 27 (12):2659-2662. doi: 10.1088/0022-3727/27/12/030
12. Becker FF, Wang X B, Huang Y, Pethig R, Vykoukal J, Gascoyne PRC (1995) Separation Of Human Breast-Cancer Cells From Blood By Differential Dielectric Affinity. Proceedings of the National Academy of Sciences of the United States of America 92 (3):860-864
13. Burt JPH, Pethig R, Gascoyne PRC, Becker FF (1990) Dielectrophoretic Characterization Of Friend Murine Erythroleukaemic Cells As A Measure Of Induced-Differentiation. Biochimica Et Biophysica Acta 1034 (1):93-101
14. Wang XB, Huang Y, Gascoyne PRC, Becker FF, Holzel R, Pethig R (1994) Changes In Friend Murine Erythroleukemia Cell-Membranes During Induced-Differentiation Determined By Electrorotation. Biochimica et Biophysica Acta-Biomembranes 1193 (2):330-344
15. Petr J, Maier V (2012) Analysis of microorganisms by capillary electrophoresis. Trac-Trends in Analytical Chemistry 31:9-22. doi:10.1016/j.trac.2011.07.013
16. Armstrong DW, Schulte G, Schneiderheinze JM, Westenberg DJ (1999) Separating microbes in the manner of molecules. 1. Capillary electrokinetic approaches. Anal Chem 71 (24):5465-5469. doi:10.1021/ac990779z
17. Srivastava SK, Daggolu PR, Burgess SC, Minerick AR (2008) Dielectrophoretic characterization of erythrocytes: Positive ABO blood types. Electrophoresis 29 (24):5033-5046. doi:10.1002/elps.200800166
18. Chou CF, Tegenfeldt JO, Bakajin O, Chan SS, Cox EC, Darnton N, Duke T, Austin RH (2002) Electrodeless dielectrophoresis of single- and double-stranded DNA. Biophysical Journal 83 (4):2170-2179
19. Cummings E, Singh A (2003) Dielectrophoresis in microchips containing arrays of insulating posts: Theoretical and experimental results. Anal Chem 75 (18):4724-4731. doi:10.1021/ac0340612
20. Pysher MD, Hayes MA (2007) Electrophoretic and dielectrophoretic field gradient technique for separating bioparticles. Anal Chem 79 (12):4552-4557. doi:10.1021/ac070534j
21. Mack C (2007) Fundamental Principles of Optical Lithography: The Science of Microfabrication. John Wiley and Sons Ltd, Chichester, West Sussex, England
22. Staton SJR, Jones PV, Ku G, Gilman SD, Kheterpal I, Hayes MA (2012) Manipulation and capture of A beta amyloid fibrils and monomers by DC insulator gradient dielectrophoresis (DC-iGDEP). Analyst 137 (14):3227-3229. doi:Doi 10.1039/C2an35138b
23. Hsiao AP, Barbee KD, Huang X (2010) Microfluidic device for capture and isolation of single cells.77590W-77590W. doi:10.1117/12.861563
24. Preira P, Grandne V, Forel JM, Gabriele S, Camara M, Theodoly O (2013) Passive circulating cell sorting by deformability using a microfluidic gradual filter. Lab on a Chip 13 (1):161-170. doi:10.1039/c21c40847c
25. Phillips JA, Xu Y, Xia Z, Fan ZH, Tan WH (2009) Enrichment of Cancer Cells Using Aptamers Immobilized on a Microfluidic Channel. Anal Chem 81 (3):1033-1039. doi:10.1021/ac802092j
26. Olitzki L (1932) Electric charge of bacterial antigens. Journal of Immunology 22 (4):251-256
27. Jones PV, Staton SJR, Hayes MA (2011) Blood cell capture in a sawtooth dielectrophoretic microchannel. Analytical and Bioanalytical Chemistry 401 (7):2103-2111. doi:Doi 10.1007/S00216-011-5284-9
28. Chen KP, Pacheco JR, Hayes MA, Staton SJR (2009) Insulator-based dielectrophoretic separation of small particles in a sawtooth channel. Electrophoresis 30 (9):1441-1448. doi:10.1002/elps.200800833
29. Hamadi F, Latrache H, Zahir H, Elghmari A, Timinouni M, Ellouali M (2008) The relation between *Escherichia coli* surface functional groups' composition and their physicochemical properties. Brazilian Journal of Microbiology 39 (1):10-15. doi:10.1590/s1517-83822008000100003

30. Amory DE, Mozes N, Hermesse MP, Leonard AJ, Rouxhet PG (1988) Chemical-analysis of the surface of microorganisms by X-ray photoelectron-spectroscopy. Fems Microbiology Letters 49 (1):107-110. doi:10.1111/j.1574-6968.1988.tb02690.x 31. El Ghmari A, Latrache H, Hamadi F, El Louali M, El Bouadili A, Hakkou A, Bourlioux P (2002) Influence of surface cell structures on physicochemical properties of *Escherichia coli*. Microbiologica 25 (2):173-178

32. Latrache H, Mozes N, Pelletier C, Bourlioux P (1994) Chemical and physicochemical properties of *Escherichia coli*: variations among three strains and influence of culture conditions. Colloids and Surfaces B: Biointerfaces 2 (1-3):47-56. doi:http://dx.doi.org/10.1016/0927-7765(94)80017-0

33. Lytle DA, Rice EW, Johnson CH, Fox KR (1999) Electrophoretic mobilities of *Escherichia coli* O157:H7 and wild-type *Escherichia coli* strains. Applied and Environmental Microbiology 65 (7):3222-3225

34. Pethig R (2010) Dielectrophoresis: Status of the theory, technology, and applications (vol 4, 022811, 2010). Biomicrofluidics 4 (3). doi:10.1063/1.3474458

35. Castellarnau M, Errachid A, Madrid C, Juarez A, Samitier J (2006) Dielectrophoresis as a tool to characterize and differentiate isogenic mutants of *Escherichia coli*. Biophysical Journal 91 (10):3937-3945. doi:10.1526/biophysj.106.088534

36. Weiss NG, Jones PV, Mahanti P, Chen KP, Taylor TJ, Hayes MA (2011) Dielectrophoretic mobility determination in DC insulator-based dielectrophoresis. Electrophoresis 32 (17):2292-2297. doi:Doi 10.1002/Elps.201100034

Although the foregoing specification fully discloses and enables the present invention, it is not intended to limit the scope of the invention, which is defined by the claims appended hereto.

All publications, patents and patent applications are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. An apparatus comprising:
   a punctuated microgradient device that includes:
   a substrate having a first continuous microchannel that is patterned with a plurality of sequential features to form a plurality of reservoirs including a first, second and third reservoir, and a plurality of constricted passageways including a first constricted passageway that connects the first reservoir to the second reservoir and a second constricted passageway that connects the second reservoir to the third reservoir, wherein the microchannel has walls that are electrically insulative; and
   a first electrode and a second electrode both operatively coupled to the first microchannel and configured to establish an electric field E within the microchannel, wherein the first electrode is fabricated on a first end of the first constricted passageway, wherein the first end of the first constricted passageway is in the first reservoir.

2. The apparatus of claim 1, wherein the electrical field E includes a first local electrical field $E_1$ in the first constricted passageway and a second local electrical field $E_2$ in the second constricted passageway, and wherein a magnitude of the first local electrical field $E_1$ is greater than the second local electrical field $E_2$.

3. The apparatus of claim 1, wherein the second constricted passageway has a smaller cross-sectional area than the first constricted passageway.

4. The apparatus of claim 1, wherein the second constricted passageway has a shorter length than the first constricted passageway.

5. The apparatus of claim 1, wherein the first continuous microchannel has a saw-tooth-shaped cross-section.

6. The apparatus of claim 1, wherein the first continuous microchannel has a cross-sectional shape that establishes a first local dielectrophoresis (DEP) gradient, $(d\nabla|E|^2/dx_1)_{local}$ at the first constricted passageway and a different second local dielectrophoresis (DEP) gradient, $(d\nabla|E|^2/dx_2)_{local}$ at the second constricted passageway, wherein $x_1$ is a length parameter of the first constricted passageway, $x_2$ is a length parameter of the second constricted passageway.

7. The apparatus of claim 1, wherein the first continuous microchannel has a cross-sectional shape that establishes a first local dielectrophoresis (DEP) gradient, $(d\nabla|E|^2/dx_1)_{local}$ at the first constricted passageway and a different second local dielectrophoresis (DEP) gradient, $(d\nabla|E|^2/dx_2)_{local}$ at the second constricted passageway and a global DEP gradient $$\left(\frac{d\nabla|E|^2}{dx}\right)_{global} = \frac{\left(\frac{d\nabla|E|^2}{dx_2}\right)_{local} - \left(\frac{d\nabla|E|^2}{dx_1}\right)_{local}}{\Delta x},$$

wherein $x_1$ is a length parameter of the first constricted passageway, $x_2$ is a length parameter of the second constricted passageway, and $\Delta x$ is a parameter of distance between the first constricted passageway and the second constricted passageway.

8. The apparatus of claim 1, wherein the first continuous microchannel has a cross-sectional shape that establishes a first local electrical field $E_1$ in the first constricted passageway, a second local electrical field $E_2$ in the second constricted passageway, and wherein a magnitude of the first local electrical field $E_1$ is greater than the second local electrical field $E_2$, a first local dielectrophoresis (DEP) gradient, $(d\nabla|E|^2/dx_1)_{local}$ at the first constricted passageway, and a different second local dielectrophoresis (DEP) gradient, $(d\nabla|E|^2/dx_2)_{local}$ at the second constricted passageway, and a global DEP gradient $$\left(\frac{d\nabla|E|^2}{dx}\right)_{global} = \frac{\left(\frac{d\nabla|E|^2}{dx_2}\right)_{local} - \left(\frac{d\nabla|E|^2}{dx_1}\right)_{local}}{\Delta x},$$

wherein $x_1$ is a length parameter of the first constricted passageway, $x_2$ is a length parameter of the second constricted passageway, and $\Delta x$ is a parameter of distance between the first constricted passageway and the second constricted passageway.

9. The apparatus of claim 1, wherein the first continuous microchannel has a cross-sectional shape that establishes a first ratio of electric field E to local dielectrophoresis (DEP) gradient, $(d\nabla|E|^2/dx_1)_{local}$ at the first constricted passageway that is different than a second ratio of electric field E to local dielectrophoresis (DEP) gradient, $(d\nabla|E|^2/dx_2)_{local}$ at the second constricted passageway, wherein $x_1$ is a length parameter of the first constricted passageway, and wherein $x_2$ is a length parameter of the second constricted passageway.

10. The apparatus of claim 1, wherein the first continuous microchannel includes a plurality of constricted passageways formed in parallel between each successive pair of reservoirs of the plurality of reservoirs in order to increase the amount of the species collected and concentrated in each one of the plurality of reservoirs, including a third constricted passageway that is in parallel to the first constricted passageway between the first reservoir and the second reservoir, and a fourth constricted passageway that is in parallel to the second constricted passageway between the second reservoir and the third reservoir.

11. The apparatus of claim 1, wherein the first continuous microchannel includes a plurality of constricted passageways formed in parallel between each successive pair of reservoirs of the plurality of reservoirs in order to increase the amount of the species collected and concentrated in each one of the plurality of reservoirs, including a third constricted passageway that is in parallel to the first constricted passageway between the first reservoir and the second reservoir, and a fourth constricted passageway that is in parallel to the second constricted passageway between the second reservoir and the third reservoir.

12. The apparatus of claim 1, further comprising one or more additional electrodes operatively coupled to the first microchannel along the length of the first microchannel between the first electrode and the second electrode.

13. The apparatus of claim 1, further comprising a pump connected to apply a pressure difference between the first reservoir and a last reservoir of the first microchannel in order to urge a flow of material through the first microchannel.

14. The apparatus of claim 1, wherein the apparatus is configured to establish different dielectrophoretic gradients at each of the plurality of constricted passageways along the first microchannel.

15. The apparatus of claim 1, wherein the apparatus includes a plurality of microchannels, each substantially the same as the first microchannel, fabricated in a single substrate.

16. A method of separating particles, the method comprising:
providing a substrate having a first continuous microchannel that is patterned with a plurality of sequential, constrictive insulating features to form a plurality of reservoirs including a first, second and third reservoir, and a plurality of constricted passageways including a first constricted passageway that connects the first reservoir to the second reservoir and a second constricted passageway that connects the second reservoir to the third reservoir, wherein the microchannel has walls that are electrically insulative; and
applying a first local electrical field $E_1$ in the first constricted passageway and a second local electrical field $E_2$ in the second constricted passageway, wherein a magnitude of the first local electrical field $E_1$ is greater than the second local electrical field $E_2$, wherein the first electrode is on a first end of the first constricted passageway, and wherein the first end of the first constricted passageway is in the first reservoir.

17. The method of claim 16, wherein the second constricted passageway has a smaller cross-sectional area than the first constricted passageway.

18. The method of claim 16, wherein the second constricted passageway has a shorter length than the first constricted passageway.

19. The method of claim 16, wherein the first continuous microchannel has a saw-tooth-shaped cross-section.

20. The method of claim 16, further comprising establishing a first local dielectrophoresis (DEP) gradient, $(d\nabla|E|^2/dx_1)_{local}$ at the first constricted passageway and a different second local dielectrophoresis (DEP) gradient, $(d\nabla|E|^2/dx_2)_{local}$ at the second constricted passageway, wherein $x_1$ is a length parameter of the first constricted passageway, $x_2$ is a length parameter of the second constricted passageway.

21. The method of claim 16, further comprising establishing a first local dielectrophoresis (DEP) gradient, $(d\nabla|E|^2/dx_1)_{local}$ at the first constricted passageway and a different second local dielectrophoresis (DEP) gradient, $(d\nabla|E|^2/dx_2)_{local}$ at the second constricted passageway and a global DEP gradient $$\left(\frac{d\nabla|E|^2}{dx}\right)_{global} = \frac{\left(\frac{d\nabla|E|^2}{dx_2}\right)_{local} - \left(\frac{d\nabla|E|^2}{dx_1}\right)_{local}}{\Delta x},$$

wherein $x_1$ is a length parameter of the first constricted passageway, $x_2$ is a length parameter of the second constricted passageway, and $\Delta x$ is a parameter of distance between the first constricted passageway and the second constricted passageway.

22. The method of claim 16, further comprising establishing a first local electrical field $E_1$ in the first constricted passageway, a second local electrical field $E_2$ in the second constricted passageway, and wherein a magnitude of the first local electrical field $E_1$ is greater than the second local electrical field $E_2$, a first local dielectrophoresis (DEP) gradient, $(d\nabla|E|^2/dx_1)_{local}$ at the first constricted passageway, and a different second local dielectrophoresis (DEP) gradient, $(d\nabla|E|^2/dx_2)_{local}$ at the second constricted passageway, and a global DEP gradient $$\left(\frac{d\nabla|E|^2}{dx}\right)_{global} = \frac{\left(\frac{d\nabla|E|^2}{dx_2}\right)_{local} - \left(\frac{d\nabla|E|^2}{dx_1}\right)_{local}}{\Delta x},$$

wherein $x_1$ is a length parameter of the first constricted passageway, $x_2$ is a length parameter of the second constricted passageway, and $\Delta x$ is a parameter of distance between the first constricted passageway and the second constricted passageway.

23. The method of claim 16, wherein the first continuous microchannel has cross-section shape that establishes a first ratio of electric field E to local dielectrophoresis (DEP) gradient, $(d\nabla|E|^2/dx_1)_{local}$ at the first constricted passageway that is different than a second ratio of electric field E to local dielectrophoresis (DEP) gradient, $(d\nabla|E|^2/dx_2)_{local}$ at the second constricted passageway, wherein $x_1$ is a length parameter of the first constricted passageway, and wherein $x_2$ is a length parameter of the second constricted passageway.

* * * * *